United States Patent
Polo Pozo et al.

(10) Patent No.: US 11,690,871 B2
(45) Date of Patent: Jul. 4, 2023

(54) ANIMAL PLASMA OR FRACTIONS THEREOF FOR USE IN TREATING COGNITIVE IMPAIRMENT DISORDERS IN HUMANS AND COMPANION ANIMALS

(71) Applicant: APC EUROPE SLU, Granollers (ES)

(72) Inventors: Francisco Javier Polo Pozo, Barberá del Vallés (ES); Louis Edward Russell, Ankeny, IA (US); María Carmen Rodríguez Canel, Barcelona (ES); Joy Marlene Campbell, Ames, IA (US); Joe David Crenshaw, Windsor Heights, IA (US); Miquel Moretó Pedragosa, Esplugues del Llobregat (ES); Anna Pérez Bosque, Igualada (ES); Lluïsa Miró Martí, Barcelona (ES)

(73) Assignee: APC EUROPE SLU, Barcelona (ES)

( * ) Notice: Subject to any disclaimer, the term of this patent is extended or adjusted under 35 U.S.C. 154(b) by 712 days.

(21) Appl. No.: 16/613,951

(22) PCT Filed: May 17, 2018

(86) PCT No.: PCT/EP2018/062915
§ 371 (c)(1),
(2) Date: Nov. 15, 2019

(87) PCT Pub. No.: WO2018/211014
PCT Pub. Date: Nov. 22, 2018

(65) Prior Publication Data
US 2021/0260112 A1 Aug. 26, 2021

(30) Foreign Application Priority Data

May 18, 2017 (ES) ............... ES201730705

(51) Int. Cl.
| | |
|---|---|
| A61K 35/16 | (2015.01) |
| A61P 25/28 | (2006.01) |
| A61K 35/57 | (2015.01) |
| A61K 38/17 | (2006.01) |
| A61K 38/40 | (2006.01) |

(52) U.S. Cl.
CPC ............. *A61K 35/16* (2013.01); *A61K 35/57* (2013.01); *A61K 38/1703* (2013.01); *A61K 38/1722* (2013.01); *A61K 38/1741* (2013.01); *A61K 38/1774* (2013.01); *A61K 38/40* (2013.01); *A61P 25/28* (2018.01)

(58) Field of Classification Search
None
See application file for complete search history.

(56) References Cited

U.S. PATENT DOCUMENTS

| | | |
|---|---|---|
| 2015/0157664 A1 | 6/2015 | Wyss-Coray et al. |
| 2016/0235786 A1 | 8/2016 | Hughes |

FOREIGN PATENT DOCUMENTS

| | | |
|---|---|---|
| EP | 2149380 A1 | 2/2010 |
| WO | 2004078187 A1 | 9/2004 |

OTHER PUBLICATIONS

Anderson, et al., "The Human Plasma Proteome: History, character, and diagnostic prospects", Molecular & Cellular Proteomics, 2002, 1(11), pp. 845-867.
Anonymous, "Blood basics:Physical properties of blood and plasma", XP055485223, retrieved on Nov. 14, 2019, www.sigmaaldrich.com/life-science/metabolomics/enzyme-explorer/learning-center/plasma-blood-protein/blood-basics.printerview.html.
Brodaty, et al., "What is the best dementia screening instrument for general practitioners to use?", Am J Geriatr Psychiatry, 2006, 14(5), pp. 391-400.
Coffey, et al., "Use of spray-dried animal plasma in diets for weanling pigs", Pig News Info, 2001, 22, 3 pages.
Gao, et al., "Effects of spray-dried animal plasma on serous and intestinal redox status and cytokines of neonatal pigs", J. Anim. Sci., 2011, 89, pp. 150-157.
Gisbert, et al., "Spray-dried plasma promotes growth, modulates the activity of antioxidant defenses, and enhances the immune status of gilthead sea bream (*Sparus aurata*) fingerlings", J. Anim. Sci., 2015, 93, pp. 278-286.
Heckler, et al., "Clinical feasibility of cognitive testing in dogs (*Canis lupus familiaris*)", J. Vet. Behavior, 2014, 9, pp. 6-12.
International Search Report (PCT/ISA/210) and Written Opinion (PCT/ISA/237) dated Jul. 5, 2018, by the European Patent Office as the International Searching Authority for International Application No. PCT/EP2018/062915.

(Continued)

*Primary Examiner* — Thane Underdahl

(74) *Attorney, Agent, or Firm* — Panitch Schwarze Belisario & Nadel LLP

(57) ABSTRACT

The present application relates to the administration of plasma, fractions thereof, or mixtures thereof to humans or animals to treat or otherwise improve cognitive impairment disorders, including dementia (e.g., vascular dementia, dementia with Lewy bodies, dementia resulting from Alzheimer's disease, dementia resulting from Parkinson's disease, frontotemporal dementia, and dementia resulting from normal pressure hydrocephalus in humans, and cognitive dysfunction syndrome in companion animals), concussion, and traumatic brain injury. In certain embodiments, the invention comprises a method of treating a cognitive impairment disorder in a human or companion animal subject, said method comprising: administering to said subject one or more cognitive functioning tests to identify a subject suffering from a cognitive impairment disorder; and administering to said subject a therapeutically effective amount of an animal plasma composition; wherein said administration provides an improvement in said subject's results in said one or more cognitive impairment tests.

27 Claims, 13 Drawing Sheets

(56) References Cited

OTHER PUBLICATIONS

Kiraly, et al., "Traumatic brain injury and delayed sequelae: a review—traumatic brain injury and mild traumatic brain injury (concussion) are precursors to later-onset brain disorders, including early-onset dementia", TheScientificWorldJournal, 2007, 7, pp. 1768-1776.
Maijó, et al., "Dietary plasma proteins attenuate the innate immunity response in a mouse model of acute lung injury", British Journal of Nutrition, 2012, 107, pp. 867-875.
Maijó, et al., "Dietary plasma proteins modulate the adaptive immune response in mice with acute lung inflammation", Journal of Nutrition, 2012, 142, pp. 264-270.
Moretó, et al., "Dietary plasma proteins, the intestinal immune system, and the barrier functions of the intestinal mucosa", J. Anim. Sci., 2009, 87, pp. E92-E100.
Peace, et al., "Spray-dried porcine plasma influences intestinal barrier function, inflammation and diarrhea in weaned pigs", J. Nutr., 2011, 141, pp. 1312-1317.
Petschow, et al. "Serum-derived bovine immunoglobulin/protein isolate: postulated mechanism of action for management of enteropathy", Clin Exp Gastroenterol, 2014, 7, pp. 181-190.
Shively, et al., "Dementia resulting from traumatic brain injury: what is the pathology?", Arch. Neurol., 2012, 69(10), pp. 1245-1251.
Torrallardona, "Spray-dried animal plasma as an alternative to antibiotics in weanling pigs: a review", Asian-Aust. J. Anim. Sci., 2010, vol. 23, No. 1, pp. 131-148.
Xiong, et al., "Animal models of traumatic brain injury", Nature reviews Neuroscience, Feb. 2013, 14(2), pp. 128-142.

ANIMAL PLASMA OR FRACTIONS THEREOF FOR USE IN TREATING COGNITIVE IMPAIRMENT DISORDERS IN HUMANS AND COMPANION ANIMALS

CROSS-REFERENCE TO RELATED APPLICATIONS

The present application claims priority to Spanish Patent Application No. P201730705, filed on May 18, 2017, which is incorporated herein by reference in its entirety for all purposes.

FIELD OF THE INVENTION

The present application relates to the administration of plasma, fractions thereof, or mixtures thereof to humans or animals to treat or otherwise improve cognitive impairment disorders, including dementia (e.g., vascular dementia, dementia with Lewy bodies [DLB], dementia resulting from Alzheimer's disease [ADD], dementia resulting from Parkinson's disease [PDD], frontotemporal dementia, and dementia resulting from normal pressure hydrocephalus [NDHD] in humans, and cognitive dysfunction syndrome (CDS) in companion animals), concussion, and traumatic brain injury (TBI).

STATE OF THE ART

Whole blood contains various types of cells that are suspended in an extracellular matrix. If cellular material is removed from whole blood (e.g., by centrifuging whole blood in the presence of an anticoagulant), the remaining liquid (i.e., the extracellular matrix of whole blood) is the plasma portion. Plasma is composed mainly of water and dissolved proteins, the majority of which are albumins, globulins, and fibrinogen. Various protein fractions and/or components can be purified from plasma using methods that are well known and commonly practiced by those of ordinary skill in the art. One such method involves spray-drying of plasma separated from animal blood to produce a dried composition of plasma proteins, referred to herein as spray-dried plasma (SDP). Spray-dried plasma consists primarily of albumin and globulins, along with lesser quantities of other proteins or peptides. As used herein, unless otherwise indicated, the terms "plasma," "plasma proteins," and "SDP" encompass blood plasma and/or any protein fractions and/or components which may be further purified therefrom.

Several peer reviewed research studies have demonstrated a beneficial impact on immune response and immune and gut function in animals fed plasma proteins, such as SDP. For example, studies involving challenge or natural infection with pathogenic bacteria, viruses, or protozoa have reported reduced mortality and/or improved healthy indices in a variety of species (humans, swine, calves, poultry, and shrimp) fed diets containing plasma proteins, such as SDP-supplemented diets. (Torrallardona et al., 2010; Petschow et al., 2014; Gisbert et al., 2015). Although spray-dried plasma contains globulin protein, antibody neutralization of antigens in the gut lumen does not fully explain the improvements noted in animals fed with plasma proteins. Several recent studies have also reported altered immune response in mucosal tissue of animals fed diets supplemented with SDP. (Moretó and Pérez-Bosque, 2009; Peace et al., 2011; Gao et al., 2010; Maijó et al., 2011, 2012). Additionally, SDP supplementation is common in nursery pig feed during the post-weaning period, and published research shows that addition of SDP to pig diets at weaning increases feed intake, growth rate, and improves feed efficiency. (Coffey and Cromwell, 2001; Van Dijk et al., 2001; Torrallardona, 2010).

Numerous cognitive impairment disorders are prevalent in humans and animals today, including dementia, concussion, and traumatic brain injury (TBI). (Brodaty et al., 2006; Kiraly and Kiraly, 2007; Shively et al., 2012; Xiong et al., 2013; WHO, 2016; Heckler et al., 2014).

Dementia refers to a category of brain diseases that result in a long-term, and frequently gradual, decrease in cognitive functioning. As dementia becomes more severe, it may affect the subject's ability to think and remember to the point that it impacts daily functioning. Dementia can result from numerous diseases or disorders, including vascular dementia, dementia with Lewy bodies (DLB), dementia resulting from Alzheimer's disease (ADD), dementia resulting from Parkinson's disease (PDD), frontotemporal dementia, dementia resulting from normal pressure hydrocephalus (NDHD), and cognitive dysfunction syndrome (CDS). Though each of these causative diseases/disorders is distinct, the resulting dementia is similar.

Vascular dementia, also referred to as multi-infarct dementia, is the second most common cause of dementia in older humans, behind Alzheimer's disease. Vascular dementia effectively results from a lack of oxygen and/or nutrients to the brain's nerve cells due to a reduced flow of blood to areas of the brain. The decreased blood flow generally results from blocked or narrowed blood vessels that can cause a series of relatively minor strokes.

Alzheimer's disease is the most common cause of human dementia and its incidence is rising, affecting roughly 10% of the population over 65 and 40% of those over 85 years. It is currently an irreversible disease. The initiating factor, which appears necessary but not sufficient for Alzheimer's disease, is the accumulation of amyloid aggregates consisting of the Aβ peptide (42 amino acids in length). Evidence is now emerging that these amyloid deposits may be present up to a decade prior to the initiation of cognitive symptoms of the disorder. A second step in the pathogenesis of the disease is the formation of intraneuronal neurofibrillary tangles formed from hyperphosphorylated forms of the microtubule binding protein tau. AD is commonly preceded by a condition called mild cognitive impairment, which is characterized by mild memory loss with preservation of other cognitive and functional activities Cognitive dysfunction syndrome (CDS) in companion animals, such as dogs and cats, is an alteration characterized by a decline in cognitive function in elderly animals. This progressive neurodegenerative disorder has similar features to AD. Several cognitive tests have been developed to evaluate particular aspects of animal learning and memory, which can be employed in the detection, identification, and diagnosing of CDS. Using these tests, the onset of decline in learning and memory has been demonstrated in dogs as young as 7 years of age, however, CDS clinical cases are rarely detected until the age of 11 years or older in dogs. Elderly animals may present learning impairment and decline in performance in activities that require memory, as well as behavioral changes.

Concussion, also referred to as mild traumatic brain injury, is a head injury with a temporary impairment of some brain function caused by minor trauma to the head. Concussions are often the result of a blow to the head, such as those resulting from sports injuries, car accidents, or falls, but can also result from acceleration/deceleration forces without a direct impact. Concussions can result in a variety of physical, cognitive, and/or emotional symptoms, which can vary from very mild to relatively severe. Symptoms that can accompany a concussion include loss of consciousness, headache, dizziness, vomiting, nausea, lack of motor coordination, loss of balance, light sensitivity, blurred vision, ringing in the ears, confusion/disorientation, difficulty focusing/paying attention, amnesia, incoherent speech, behavioral changes, sleep disturbance, and behavioral changes, such as irritability. Symptoms typically last several weeks, though they can persist for extended periods of time. Current treatment for concussion typically involves physical and cognitive rest and monitoring of symptoms.

Traumatic brain injury (TBI) is damage to the brain resulting from external force, such as rapid acceleration/deceleration, impact, blast waves, or penetration by a projectile. Brain function in a subject suffering TBI is temporarily or permanently impaired, though physical damage to the brain may or may not be apparent. TBI can be classified by level of severity—either mild, moderate, or severe—based on a number of factors, such as the Glasgow Coma Scale (which measures level of consciousness based on several factors), duration of post-traumatic amnesia, and/or duration of loss of consciousness. Severity of TBI can also be classified by physical or pathological features, such as severity of brain swelling and existence and locations of focal and/or diffuse brain lesions. Symptoms of TBI vary depending on the severity of the TBI and the type and location of the injury to the brain. Common symptoms include loss of consciousness (which can last from just a few seconds to >24 hours), headache, dizziness, vomiting, nausea, lack of motor coordination, loss of balance, light sensitivity, blurred vision, ringing in the ears, confusion/disorientation, difficulty focusing/paying attention, amnesia, incoherent speech, behavioral changes, sleep disturbance, dilation of pupil(s), aphasia, dysarthria, slurred speech, weakness/numbness in the limbs, convulsions, and behavioral changes, such as irritability. Long-term symptoms of moderate to severe TBI include deficits in social judgment, alexithymia, attention deficits, and reduced cognitive processing speed. Long-term treatment for moderate to severe TBI generally focuses on rehabilitation aimed at improving independent function at home and in society and helping the affected individual adapt to any long-term disabilities that exist.

Neuroglia make up about half the volume of the CNS. The cells that we can found are astrocytes, oligodendrocytes, microglia cells, and ependymal cells. Astrocytes are thought to play a number of active roles in the brain, including the secretion of neural transmitters and the maintenance of the blood-brain barrier. Microglial cells function as phagocytes, remove cellular debris formed during normal development of the nervous system, phagocytize microbes, and eliminate the damaged tissue. The microglia is the primary site for brain β-amyloid peptide (Aβ) clearance and plays and important role in the neuronal homeostasis and synaptic plasticity Early detection/diagnosis of cognitive impairment disorders, such as dementia, concussion, and TBI, can help to reduce the ultimate severity of the symptoms, reduce recovery time, and/or slow or prevent the onset of certain symptoms. For example, if diagnosed early, available pharmaceutical treatments may slow dementia progress and reduce costs through delayed nursing home placement. See, e.g., Brodaty et al., 2006. Am J Geriatr Psychiatry 14:5, May 2006.

Numerous instruments exist to detect, identify, or diagnose dementia in human subjects. Suitable diagnostic instruments are well known to persons of ordinary skill in in the art, and currently include:
1. Seven-minute screen (7-Minute Screen)
2. A Short Form of the IQCODE (Short IQCODE)
3. Abbreviated Mental Test (AMT)
4. Bowles-Langley Technology/Ashford Memory Test (BLT/Ash)
5. Cambridge Cognitive Examination (CAMCOG)
6. The CDT scored using the 10-point Sunderland scale
7. Memory Impairment Screen (MIS)
8. Mental Alternation Test (MAT)
9. Mini-Cog
10. Mini-Mental Status Examination (MMSE)
11. Short and Sweet Screening Instrument (SASSI)
12. Short Test of Mental Status (STMS)
13. The 6-Item Cognitive Impairment Test (also called The Short Blessed Test
and The Short Orientation-Memory-Concentration Test; 6CIT)
14. The General Practitioner Assessment of Cognition (GPCOG)
15. The Rowland Universal Dementia Assessment Scale (RUDAS41)
16. Time and Change Test (T&C42)

Bene and Sepulveda, 2014; Brodaty et al., 2006; Heckler et al., 2014.

By evaluating a subject using one or more of these tests or instruments, possible cognitive impairment of the subject resulting from dementia can be analyzed.

As with similar cognitive impairment disorders in humans, early detection of CDS in companion animals allows intervention during the initial phase of the degenerative process, which increases the chances for therapy. Several cognitive tests have been developed to evaluate particular aspects of animal learning and memory, which can be employed in the detection, identification, and diagnosis of CDS. Suitable diagnostic instruments are well known to persons of ordinary skill in in the art. For example, for dogs, suitable cognitive evaluation tests may include analyses of one or more of reward and object approach learning, object discrimination learning, and reversal learning. These types of learning, and short term memory associated with them, can be evaluated using delayed-type tests, such as the delayed matched to position (DMP), delayed non-matched to position (DNMP), delayed matched to sample (DMS), and delayed non-matched to sample (DNMS) tests, all of which are well known and routinely employed by persons of ordinary skill in the art. By evaluating an animal subject's performance on one or more of these tests, possible cognitive impairment of the animal subject can be analyzed.

Each of these can be evaluated using an apparatus that contains a base with 3 wells for the positioning of reward (e.g., a small piece of food) and objects, as well as a frame with a canvas curtain to avoid the dogs' eye contact with the experimenter, the reward, and the objects during the preparation of the tests (to avoid visual cues), which is raised by a pulley system when the animal is expected to respond to the test. The wells and objects are smeared with food to avoid olfactory cues, and the apparatus is positioned some distance away from the dog to allow focus on the object. The objects are also positioned quietly to avoid auditory cues. Depending on where the reward is placed during the test, the subject's ability to learn through a distinct type of learning can be analyzed.

To evaluate reward approach learning, a reward is placed in one of the lateral wells, but mimicry is performed on both sides, and the animal's approach to only the reward side is considered a correct response. To evaluate object approach learning, an object is placed over the food (with no visual contact by the use of the curtain), and the animal's approach to only the object side is considered a correct response. To evaluate object discrimination learning, two distinct objects (e.g., objects of different colors and/or shapes) are randomly placed, and the animal should learn to approach only one of the presented objects to obtain the reward. To evaluate reversal learning, the object discrimination learning test is repeated, but previous nonrewarded object in discrimination learning is linked to the food, and the animal should learn to approach the new reward object.

For each of the delayed-type tests, a trial consists of two presentations separated by a delay to test the animal's ability to learn and retain that learned knowledge for a given duration. For example, in the DMP test performed on a dog, a reward can be placed under an object on one side (without visual contact). After the dog obtains the reward, a curtain is positioned and a 10-second delay is initiated. After this delay, two identical objects are placed in front of the dog and the dog is expected to find the reward in the previously rewarded position. In the DNMP test, during the second presentation, the dog is instead expected to find the reward in the previously non-rewarded position. In the DMS test, a reward is placed under a sample object in the central well (without visual contact). After the dog obtains the reward, a 10-second delay is initiated in which the object is outside of the animal's visual field, then both the original and a new object are presented in lateral random positions, and the dog is expected to locate the food under the original object. In the DNMS test, during the second presentation, the dog is instead expected to find the reward under the new object.

Similarly, numerous well-known diagnostic instruments exist to detect, identify, or diagnose concussion, and a person of ordinary skill in the art could readily select an appropriate instrument. For example, the ImPACT test is currently a widely-used diagnostic test that is specifically designed for the management of sports-related concussion. ImPACT measures cognitive functioning, such as verbal, visual, and working memory; visual processing speed; reaction time; and cognitive efficiency. Other diagnostic methods that are currently used to identify concussion include the Standardized Concussion Assessment Tool (SCAT1 or SCAT2), clinical exam, balance testing, concussion grading scale, computerized neurocognitive testing, and the Standardized Assessment of Concussion (SAC). By evaluating a subject using one or more of these tests, possible cognitive impairment of the subject can be analyzed.

There remains a need in the art for improved treatments for cognitive impairment disorders.

SUMMARY OF THE INVENTION

In one aspect the present application relates to a method of treating a cognitive impairment disorder in a human or companion animal subject, said method comprising:
 a. administering to said subject one or more cognitive functioning tests to identify a subject suffering from a cognitive impairment disorder; and
 b. administering to said subject a therapeutically effective amount of an animal plasma composition;
wherein said administration provides an improvement in said subject's results in said one or more cognitive impairment tests.

In another aspect the present application relates to a method of treating a cognitive impairment disorder in a human or companion animal subject, said method comprising:
 a. administering to said subject one or more cognitive functioning tests to identify a subject suffering from a cognitive impairment disorder; and
 b. administering to said subject a therapeutically effective amount of an animal plasma composition:
wherein said animal plasma composition is administered orally, and
wherein said administration provides an improvement in said subject's results in said one or more cognitive impairment tests.

In certain embodiments the animal plasma composition is derived from animal plasma from one or more animals selected from the group consisting of porcine, bovine, ovine, equine, and avian animals.

In certain embodiments, the animal plasma composition is administered at a dose of 5 mg to 100 g per day. In further embodiments, the animal plasma composition is administered at a dose of 50 mg to 50 g per day. In additional embodiments, the animal plasma composition is administered at a dose of 100 mg to 10 g per day. In still further embodiments, the animal plasma composition is administered at a dose of 500 mg to 5 g per day.

In certain embodiments, the animal plasma composition is administered at a dose of 10 mg to 1 g per kg of body weight of the animal to be treated per day. In further embodiments, the animal plasma composition is administered at a dose of 10-500 mg per kg of body weight of the animal to be treated per day. In additional embodiments, the animal plasma composition is administered at a dose of 15-200 mg per kg of body weight of the animal to be treated per day. In still further embodiments, the animal plasma composition is administered at a dose of 25-100 mg per kg of body weight of the animal to be treated per day.

In certain embodiments, the animal plasma composition is administered for at least 3 months. In other embodiments, the animal plasma composition is administered for at least 6 months. In further embodiments, the animal plasma composition is administered for at least 9 months. In additional embodiments, the animal plasma composition is administered for at least 12 months.

In certain embodiments, the cognitive impairment disorder is selected from the group consisting of dementia disorders, concussion, and traumatic brain injury. In particular embodiments, the cognitive impairment disorder is a concussion. In other embodiments the cognitive impairment disorder is a traumatic brain injury. In further embodiments, the cognitive impairment disorder is a dementia disorder. In additional embodiments, the impairment disorder is dementia resulting from Alzheimer's disease. In further embodiments, the cognitive impairment disorder is dementia resulting from Parkinson's disease. In still further embodiments, the cognitive impairment disorder is vascular dementia.

In certain embodiments, the subject is a companion animal selected from the group consisting of canine, feline, or equine. In other embodiments, the subject is a human.

In certain embodiments, the animal plasma composition is administered as a pharmaceutically acceptable aerosol. In other embodiments, the pharmaceutically acceptable aerosol is administered through a nebulizer. In further embodiments, the animal plasma composition is administered orally. In additional embodiments, the animal plasma composition is administered in food.

Oral administration, including administration in food, conveys certain unexpected results over administration through injection, e.g., intravenously or subcutaneously. When compounds, including proteins, are administered orally, they encounter the digestive system of the subject, which would generally be expected to degrade the ingested products, for example by degrading proteins into smaller peptides, such as peptide fragments, dipeptides, tripeptides, or even singular amino acids (or some combination of these smaller peptides). Thus, a therapeutic product, such as an antibody or therapeutic protein product, that can be effectively administered through an injectable route (e.g., intravenously or subcutaneously) often cannot be effectively administered orally due to the degradation of the therapeutic product in the subject's digestive system. Yet the present inventors have unexpectedly found that the protein products described herein can be effectively and therapeutically delivered orally.

In certain embodiments, the improvement in said subject's results in said one or more cognitive impairment tests comprises improved short term memory. In other embodiments, the improvement in said subject's results in said one or more cognitive impairment tests comprises improved long term memory.

In certain embodiments, the animal plasma composition comprises 70-90% by weight protein. In particular embodiments, the animal plasma composition comprises:
a. about 1.0-6.0%, about 1.4-5.6%, about 2.0-3.5%, about 2.5-3.0%, about 2.7-2.9%, or about 2.8% by weight alpha-2 macroglobulin;
b. about 1.0-5.5%, about 1.3-5.2%, about 1.8-3.3%, about 2.0-3.0%, about 2.5-2.7%, or about 2.6% by weight transferrin:
c. about 0.1-1.0%, about 0.18-0.76%, about 0.2-0.55%, about 0.3-0.45%, about 0.36-0.40%, or about 0.38% by weight vitamin-D binding protein:
d. about 0.1-2.0%, about 0.4-1.6%, about 0.5-1.2%, about 0.7-0.9%, or about 0.8% by weight alpha-1-glycoprotein:
e. about 5-30%, about 7-28%, about 10-20%, about 12-16%, or about 14% by weight IgG:
f. about 1.0-6.0%, about 1.25-5.0%, about 1.5-3.25%, about 2.0-3.0%, about 2.3-2.7%, or about 2.5% by weight IgA;
g. about 0.5-5.0%, about 0.6-4.0%, about 0.75-3.0%, about 1.0-2.0%, about 1.3-1.7%, or about 1.5% by weight of IgM; and
h. about 25-80%, about 30-70%, about 35-60%, about 40-50%, about 4248%, or about 45% by weight albumin.

In other particular embodiments, the animal plasma composition comprises:
a. 2.0-3.5% by weight alpha-2 macroglobulin;
b. 2.0-3.0% by weight transferrin:
c. 0.3-0.45% by weight vitamin-D binding protein;
d. 0.5-1.2% by weight alpha-1-glycoprotein;
e. 10-20% by weight IgG:
f. 1.5-3.25% by weight IgA:
g. 0.75-3.0% by weight of IgM; and
h. 40-50% by weight albumin.

In certain embodiments, the animal plasma composition comprises 90-95% by weight protein. In particular embodiments, the animal plasma composition comprises:
a. about 1.0-9.0%, about 2.0-8.0%, about 3.0-6.0%, about 3.5-5.0%, about 3.7-4.3%, or about 4.0% by weight alpha-2 macroglobulin:
b. about 2-18%, about 3-15%, about 3.5-12%, about 4-10%, about 5-9%, about 6-8%, or about 7% by weight transferrin;
c. about 0.1-1.0%, about 0.2-0.8%, about 0.25-0.6%, about 0.3-0.5%, about 0.38-0.42%, or about 0.4% by weight vitamin-D binding protein:
d. about 0.1-2.0%, about 0.35-1.5%, about 0.4-1.3%, about 0.5-1.1%, about 0.6-0.8%, or about 0.7% by weight alpha-1-glycoprotein:
e. about 25-75%, about 30-75%, about 35-70%, about 40-65%, about 45-62%, about 50-60%, or about 55% by weight IgG;
f. about 1.0-6.0%, about 1.25-5.00%, about 1.5-3.25%, about 2.0-3.00%, about 2.3-2.7%, or about 2.5% by weight IgA;
g. about 2.5-10%, about 3-9%, about 3.25-8%, about 3.5-7%, about 4-6%, about 4.5-5.5, or about 5% by weight of IgM; and
h. about 2.5-25%, about 5-20%, about 7-15%, about 8-12%, about 9-11%, or about 10% by weight albumin.

In other particular embodiments, the animal plasma composition comprises:
a. 3.0-6.0% by weight alpha-2 macroglobulin;
b. 4-10% by weight transferrin;
c. 0.25-0.6% by weight vitamin-D binding protein:
d. 0.4-1.3% by weight alpha-1-glycoprotein:
e. 40-65% by weight IgG:
f. 1.5-3.25% by weight IgA:
g. 3.5-7% by weight of IgM; and
h. 7-15% by weight albumin.

In another aspect, the present application relates to animal plasma, fractions thereof, or a mixture thereof for use in treating a human or a companion animal diagnosed to have a cognitive impairment disorder by an available test. Preferably said animal plasma, fractions thereof, or a mixture thereof is orally administered.

In certain embodiments, the cognitive impairment disorder is selected from the group consisting of dementia disorders, concussion, and traumatic brain injury.

In certain embodiments, the animal plasma, fractions thereof, or a mixture thereof is used in treating a dementia disorder in a human or a companion animal diagnosed to have a cognitive impairment disorder by an available test. In particular embodiments, the animal plasma, fractions thereof, or a mixture thereof is used in treating senile dementia in a human or a companion animal diagnosed to have a cognitive impairment disorder by an available test. In other particular embodiments, the animal plasma, fractions thereof, or a mixture thereof is used in treating Alzheimer disease in a human or a companion animal diagnosed to have a cognitive impairment disorder by an available test. In further particular embodiments, the animal plasma, fractions thereof, or a mixture thereof is used in treating vascular dementia in a human or a companion animal diagnosed to have a cognitive impairment disorder by an available test. In additional particular embodiments, the animal plasma, fractions thereof, or a mixture thereof is used in treating dementia resulting from Parkinson's disease in a human or a companion animal diagnosed to have a cognitive impairment disorder by an available test. In still further particular embodiments, the animal plasma, fractions thereof, or a mixture thereof is used in treating concussion in a human or a companion animal diagnosed to have a cognitive impairment disorder by an available test. In additional particular embodiments, the animal plasma, fractions thereof, or a mixture thereof is used in treating mild traumatic brain injury (mTBI) in a human or a companion animal diagnosed to have a cognitive impairment disorder by an available test.

In certain embodiments the test selected from the group consisting of: Seven-minute screen, A Short Form of the IQCODE, Abbreviated Mental Test, Bowles-Langley Technology/Ashford Memory Test, Cambridge Cognitive Examination, The CDT scored using the 10-point Sunderland scale, Memory Impairment Screen, Mental Alternation Test, Mini-Cog, Mini-Mental Status Examination, Short and Sweet Screening Instrument, Short Test of Mental Status, The 6-Item Cognitive Impairment Test, The General Practitioner Assessment of Cognition, The Rowland Universal Dementia Assessment Scale, Time and Change Test, delayed matched to position test, delayed non-matched to position test, delayed matched to sample test, delayed non-matched to sample test, ImPACT test, Standardized Concussion Assessment Tool and Standardized Assessment of Concussion.

In particular embodiments, the animal plasma, fractions thereof, or a mixture thereof is used in treating motor activity increase in a human or a companion animal diagnosed to have a cognitive impairment disorder by an available test. In other particular embodiments, the animal plasma, fractions thereof, or a mixture thereof is used in improving short term memory in a human or a companion animal diagnosed to have a cognitive impairment disorder by an available test. In further particular embodiments, the animal plasma, fractions thereof, or a mixture thereof is used in improving long term memory in a human or a companion animal diagnosed to have a cognitive impairment disorder by an available test. In additional particular embodiments, the animal plasma, fractions thereof, or a mixture thereof is used in treating deterioration of cognitive functions in a human or a companion animal diagnosed to have a cognitive impairment disorder by an available test.

In particular embodiments the animal plasma, fractions thereof, or a mixture thereof is administered in a pharmaceutically acceptable aerosol. In other particular embodiments, the animal plasma, fractions thereof, or a mixture thereof is administered through a nebulizer. In additional particular embodiments the animal plasma, fractions thereof or a mixture thereof is administered in food.

In particular embodiments, the dose is between 5 mg to 100 g per day. In other particular embodiments, the dose is between 10 mg to 1 g per kg body weight of the human or animal to be treated per day.

In particular embodiments, the animal plasma, fractions thereof, or a mixture thereof is in dried form. In other particular embodiments, the animal plasma, fractions thereof, or a mixture thereof is in a liquid form. In further particular embodiments, the animal plasma, fractions thereof, or a mixture thereof is in a paste form.

In certain embodiments, the animal plasma, fractions thereof or a mixture thereof are derived from the group of animals formed by porcine, bovine, ovine, equine and avian.

In particular embodiments, the animal plasma, fractions thereof or a mixture thereof is a fraction of plasma or a mixture thereof that comprises at least 15% by weight of IgG. In other particular embodiments, the animal plasma, fractions thereof or a mixture thereof is a fraction of plasma or a mixture thereof that comprises 4% by weight or less of IgA.

In particular embodiments, the companion animals are animals from the group of canine, feline or equine. In other particular embodiments, the animal plasma, fractions thereof or a mixture thereof is for use in treating a human.

In particular embodiments, animal plasma, fractions thereof, or a mixture thereof, may be collected from animals of a variety of ages at the time of collection. The plasma or plasma fractions are often collected from animals of "market age," meaning the animals are at the age when they would appropriately be slaughtered, which is not exclusively animals of a young age. For example, blood from pigs at 6-8 months of age and also from sows of several years-old may be collected. In another example, bovine blood from cows of several years old may be collected. The examples provided herewith indicate that plasma, fractions thereof, or a mixture thereof, collected from animals of any age, when administered orally, have a clear effect improving cognitive functions. The examples and embodiments provided herewith are not restricted to plasma, fractions thereof, or a mixture thereof obtained exclusively from young animals.

In other embodiments the animal plasma, fractions thereof, or mixture thereof may be obtained from one species type and administered to a different species type. For example, bovine plasma may be administered to mice. It was unexpectedly and surprisingly found by the present inventors that plasma, fractions thereof, or a mixture thereof obtained from one species can be administered to an unrelated, different species and have a clear effect on improving cognitive functions, as shown in the examples provided herewith.

In certain embodiments, the animal plasma, fractions thereof, or mixture thereof is obtained from animals that have not been immunized against a particular target of interest and would not be described as hyper-immune. Instead, the animal plasma, fractions thereof, or mixture thereof is taken from animals in a naïve and/or normal immune state (not a stimulated immune state).

As disclosed in the present application, orally administrating the plasma, fractions thereof, or a mixture thereof, was surprisingly and unexpectedly found by the present inventors to improve cognitive functions. One skilled in the art would not expect oral administration to have any effect, for at least the reason that digestion of the plasma, fractions thereof, or mixture thereof would dramatically alter the composition. When compounds, including proteins, are administered orally, they encounter the digestive system of the subject, which would generally be expected to degrade the ingested products, for example by degrading proteins into smaller peptides, such as peptide fragments, dipeptides, tripeptides, or even singular amino acids (or some combination of these smaller peptides). When compounds, including proteins, are administered orally, they encounter the digestive system of the subject, which would generally be expected to degrade the ingested products, for example by degrading proteins into smaller peptides, such as peptide fragments, dipeptides, tripeptides, or even singular amino acids (or some combination of these smaller peptides). Because of this, a therapeutic product, such as an antibody or therapeutic protein product, that can be effectively administered through an injectable route (e.g., intravenously or subcutaneously) often cannot be effectively administered orally due to the degradation of the therapeutic product in the subject's digestive system. Yet the present inventors have unexpectedly found that the protein products described herein can be effectively and therapeutically delivered orally.

BRIEF DESCRIPTION OF THE FIGURES

Other advantages and features of the invention can be seen from the following description in which preferred non-limiting embodiments of the invention are described in reference to the attached drawings, where.

DETAILED DESCRIPTION OF THE INVENTION

Figure 1:
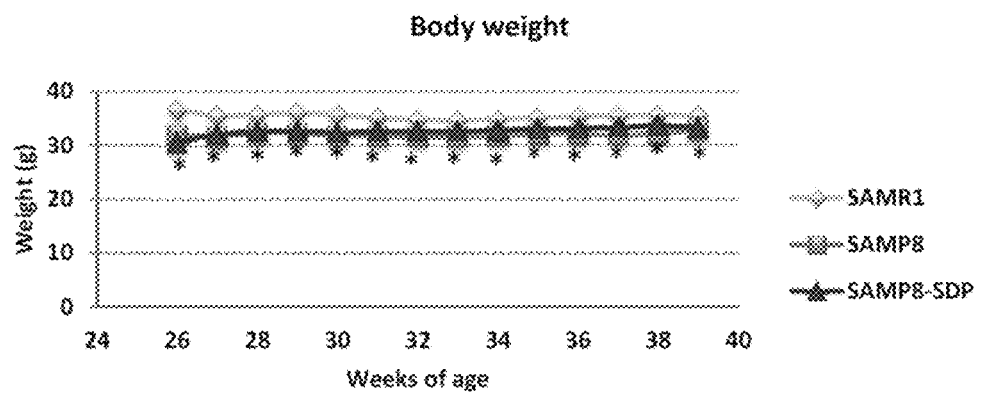
FIG. 1 provides the evolution of body weights of control (SAMR1) and experimental mice (SAMP8), with or without SDP supplementation.

Embodiments may be practiced without the theoretical aspects presented. Moreover, the theoretical aspects are presented with the understanding that the embodiments are not bound by any theory presented.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The terminology used herein is for the purpose of describing particular embodiments only and is not intended to be limiting. As used herein, the singular forms "a", "an" and "the" are intended to include plural forms as well, unless the context clearly indicates otherwise. Thus, for example, reference to "a dose" or "the dose" also includes a plurality of doses. Additionally, as used herein, the term "comprises" is intended to indicate a non-exhaustive list of components or steps, thus indicating that the given composition or method includes the listed components or steps and may also include additional components or steps not specifically listed. As an example, a core weight "comprising SBI" may also include additional components, such as flavorants, colorants, etc. The term "comprising" is also intended to encompass embodiments "consisting essentially of" and "consisting of" the listed components or steps. Similarly, the term "consisting essentially of" is also intended to encompass embodiments "consisting of" the listed components or steps. Furthermore, to the extent that the terms "including", "includes", "having", "has", "with", or variants thereof are used in either the detailed description and/or the claims, such terms are intended to be inclusive in a manner similar to the term "comprising."

Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of 10% of the referenced value. In other embodiments, the term "about" indicates that the number differs from the given number by less than 9%, 8%, 7%, 6%, 5%, 4%, 3%, 2%, or 1%.

Plasma Protein Compositions:

The present application relates to the effects of the administration of plasma protein compositions, such as SDP, on cognitive impairment. Plasma protein compositions useful in the present invention can be obtained from any suitable animal source. Preferably the animal plasma, fractions thereof or mixtures thereof are derived from the group of animals formed by porcine, bovine, ovine, equine and avian.

Various protein fractions and/or components can be purified from plasma using methods that are well known and commonly practiced by those of ordinary skill in the art. For example, globulin concentrates can be obtained by spray drying, lyophilization, or any other drying method. One preferred method involves spray-drying of plasma separated from animal blood to produce a dried composition of plasma proteins, referred to herein as spray-dried plasma (SDP). Spray-dried plasma consists primarily of albumin and globulins, along with lesser quantities of other proteins or peptides. As used herein, unless otherwise indicated, the terms "plasma," "plasma proteins," and "SDP" can be used interchangeably and encompass blood plasma and/or any protein fractions and/or components which may be further purified therefrom.

Plasma proteins used of the current application can be used in any suitable form, including both dried and liquid forms. In certain embodiments, the compositions used in this application can be in the form of tablets, capsules, ampoules for oral use, granulate powder, cream, both as a unique ingredient and associated with other excipients or active compounds, or even as a feed additive. In certain embodiments, the plasma protein compositions described herein can be provided or administered in powder form, in some instances suspended or dissolved in a suitable liquid, such as water, saline, or milk. The plasma protein composition can be combined with a pharmaceutically acceptable carrier such as a suitable liquid vehicle or excipient and an optional auxiliary additive or additives. The liquid vehicles and excipients are conventional and commercially available. Illustrative thereof are distilled water, physiological saline, aqueous solutions of dextrose, and the like. In general, in addition to the active compounds, the compositions of this invention may contain suitable excipients and auxiliaries which facilitate processing of the active compounds into preparations which can be used pharmaceutically. In certain embodiments, the plasma proteins may also be microencapsulated, thereby protecting and stabilizing them from high temperature, oxidants, pH-like humidity, etc.

In one embodiment of the invention, the plasma protein composition contains at least about 10% by weight Ig. In other embodiments, the plasma protein composition contains from about 10% to about 80% by weight Ig. In further embodiments, the plasma protein composition contains from about 12% to about 75%, from about 15% to about 70%, from about 18% to about 65%, from about 20% to about 60%, from about 22% to about 65%, or from about 25% to about 50% by weight Ig. In other embodiments of the invention, the plasma protein composition contains at least about 10%, 11%, 12%, 13%, 14%, 15%, 16%, 17%, 18%, 19%, 20%0, 21%, 22%, 23%, 24%, 25%, 26%, 27%, 28%, 29%, 30%, 35%, 40%, 45%, 50%, 55%, 60%, 65% 70%, 75%, or 80% by weight Ig. In further embodiments of the invention, the plasma protein composition contains less than about 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65% 70%, 75%, or 80% by weight Ig.

In one embodiment of the invention, the plasma protein composition contains at least about 10% by weight IgG. In other embodiments, the plasma protein composition contains from about 10% to about 80% by weight IgG. In further embodiments, the plasma protein composition contains from about 12% to about 75%, from about 15% to about 70%, from about 18% to about 65%, from about 20% to about 60%, from about 22% to about 65%, or from about 25% to about 50% by weight IgG. In other embodiments of the invention, the plasma protein composition contains at least about 10%, 11%, 12%, 13%, 14%, 15%, 16%, 17%, 18%, 19%, 20%, 21%, 22%, 23%, 24%, 25%, 26%, 27%, 280, 29%, 30%, 35%, 40%, 45%, 50%, 55%, 60%, 65% 70%, 75%, or 80% by weight IgG. In further embodiments of the invention, the plasma protein composition contains less than about 10%, 11%, 12%, 13%, 14%, 15%, 16%, 17%, 18%, 19%, 20%, 21%, 22%, 23%, 240, 25%, 260, 27%, 28%, 29%, 30%, 35%, 40%, 45%, 50%, 55%, 60%, 65% 70%, 75%, or 80% by weight IgG.

In one embodiment of the invention, the plasma protein composition contains from about 1% to about 10% by weight IgA. In other embodiments of the invention, plasma protein composition contains about 1%, 2%, 3%, 4%, 5%, 6%, 7%, 8%, 9% or 10% by weight IgA. In further embodiments of the invention, plasma protein composition contains at least about 1%, 2%, 3%, 4%, 5%, 6%, 7%, 8%, 9% or 10% by weight IgA. In still further embodiments of the invention, plasma protein composition contains less than about 1%, 2%, 3%, 4%, 5%, 6%, 7%, 8%, 9% or 10% by weight IgA. In further embodiments, the plasma protein composition contains from about 1% to about 2%, from about 1% to about 3%, from about 1% to about 4%, from about 1% to about 5%, from about 1% to about 6%, from about 1% to about 7%, from about 1% to about 8%, from about 1% to about 9%, from about 2% to about 40%, from about 2% to about 6%, from about 2% to about 8%, from about 5% to about 10%, from about 3% to about 6%, from about 3% to about 9%, or from about 8% to about 10% by weight IgA. In a further embodiment, the plasma protein composition contains about 1% by weight IgA. In a particular embodiment, the plasma protein composition contains 2% by weight or less of IgA In one embodiment of the invention, the plasma protein composition contains from about 1% to about 10% by weight IgM. In other embodiments of the invention, the plasma protein composition contains at least about 1%, 2%, 3%, 4%, 5%, 6%, 7%, 8%, 9% or 10% by weight IgM. In further embodiments of the invention, the plasma protein composition contains less than about 1%, 2%, 3%, 4%, 5%, 6%, 7%, 8%, 9%, or 10% by weight IgM. In other embodiments of the invention, the plasma protein composition contains about 1%, 2%, 3%, 4%, 5%, 6%, 7%, 8%, 9% or 10% by weight IgM. In further embodiments the plasma protein composition contains from about 1% to about 2%, from about 1% to about 3%, from about 1% to about 4%, from about 1% to about 5%, from about 1% to about 6%, from about 1% to about 7%, from about 1% to about 8%, from about 1% to about 9%, from about 2% to about 4%, from about 2% to about 6%, from about 2% to about 8%, from about 5% to about 10%, from about 3% to about 6%, from about 3% to about 9%, or from about 8% to about 10% by weight IgM. In a further embodiment, the plasma protein composition contains about 5% by weight IgM.

In one embodiment of the invention, the plasma protein composition contains from about 15% to about 80% by weight albumin. In other embodiments of the invention, the plasma protein composition contains at least about 10%, 15%, 20%, 25%, 30%, 35%, 40%, 45%, 50%, 55%, 60%, 65%, 70%, 75%, or 80% by weight albumin. In other embodiments of the invention, the plasma protein composition contains less than about 10%, 15%, 20%, 25%, 30%, 35%, 40%, 45%, 50%, 55%, 60%, 65%, 70%, 75%, or 80% by weight albumin. In further embodiments the plasma protein composition contains from about 20% to about 75%, from about 25% to about 75%, from about 30% to about 70%, from about 35% to about 65%, from about 40% to about 60%, or from about 45% to about 55% by weight albumin. In particular embodiments, the plasma protein composition comprises about 45-55% albumin by weight.

In other embodiments, the plasma protein composition comprises 65-95% by weight protein, and in further embodiments the plasma protein composition comprises 70-90% by weight protein. In certain embodiments, the protein component of the plama protein composition comprises
  a. about 1.0-6.0%, about 1.4-5.6%, about 2.0-3.5%, about 2.5-3.0%, about 2.7-2.9%, or about 2.8% by weight alpha-2 macroglobulin;
  b. about 1.0-5.5%, about 1.3-5.2%, about 1.8-3.3%, about 2.0-3.0%, about 2.5-2.7%, or about 2.6% by weight transferrin:
  c. about 0.1-1.0%, about 0.18-0.76%, about 0.2-0.55%, about 0.3-0.45%, about 0.36-0.40%, or about 0.38% by weight vitamin-D binding protein:
  d. about 0.1-2.0%, about 0.4-1.6%, about 0.5-1.2%, about 0.7-0.9%, or about 0.8% by weight alpha-1-glycoprotein;
  e. about 5-30%, about 7-28%, about 10-20%, about 12-16%, or about 14% by weight IgG;
  f. about 1.0-6.0%, about 1.25-5.0%, about 1.5-3.25%, about 2.0-3.0%, about 2.3-2.7%, or about 2.5% by weight IgA;
  g. about 0.5-5.0%, about 0.6-4.0%, about 0.75-3.0%, about 1.0-2.0%, about 1.3-1.7%, or about 1.5% by weight of IgM; and
  h. about 25-80%, about 30-70%, about 35-60%, about 40-50%, about 42-48%, or about 45% by weight albumin.

In other embodiments, the plasma protein composition comprises 80-100% by weight protein, and in further embodiments the plasma protein composition comprises 90-95% by weight protein. In certain embodiments, the protein component of the plama protein composition comprises
  a. about 1.0-9.0%, about 2.0-8.0%, about 3.0-6.0%, about 3.5-5.0%, about 3.7-4.3%, or about 4.0% by weight alpha-2 macroglobulin;
  b. about 2-18%, about 3-15%, about 3.5-12%, about 4-10%, about 5-9%, about 6-8%, or about 7% by weight transferrin:
  c. about 0.1-1.0%, about 0.2-0.8%, about 0.25-0.6%, about 0.3-0.5%, about 0.38-0.42%, or about 0.4% by weight vitamin-D binding protein;
  d. about 0.1-2.0%, about 0.35-1.5%, about 0.4-1.3%, about 0.5-1.1%, about 0.6-0.8%, or about 0.7% by weight alpha-1-glycoprotein;
  e. about 25-75%, about 30-75%, about 35-70%, about 40-65%, about 45-62%, about 50-60%, or about 55% by weight IgG;
  f. about 1.0-6.0%, about 1.25-5.0%, about 1.5-3.25%, about 2.0-3.0%, about 2.3-2.7%, or about 2.5% by weight IgA;
  g. about 2.5-10%, about 3-9%, about 3.25-8%, about 3.5-7%, about 4-6%, about 4.5-5.5, or about 5% by weight of IgM; and
  h. about 2.5-25%, about 5-20%, about 7-15%, about 8-12%, about 9-11%, or about 10% by weight albumin.

The compositions for use in the present invention are manufactured in a manner which is itself well known in the art. For example, the preparations may be made by means of conventional mixing, granulating, dragee-making, dissolving, and/or lyophilizing processes. The processes to be used will depend ultimately on the physical properties of the ingredients used and the desired form of the end product.

Suitable excipients are, in particular, fillers such as sugars for example, lactose or sucrose, mannitol or sorbitol, cellulose preparations and/or calcium phosphates, for example tricalcium phosphate or calcium hydrogen phosphate, as well as binders such as starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for examples, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose, concentrated sugar solutions may be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet or dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added. In addition to administration with conventional carriers, active ingredients may be administered by a variety of specialized delivery drug techniques which are known to those of skill in the art.

Dosage, Duration, and Subjects:

In certain embodiments, the subjects to be treated are humans and/or companion animals. In certain embodiments, the companion animals are selected from the group consisting of canine, feline, or equine animals.

"Administering" a composition may be accomplished by oral administration, injection, infusion, parenteral, intravenous, mucosal, sublingual, intramuscular, intradermal, intranasal, intraperitoneal, intraarterial, subcutaneous absorption or by any method in combination with other known techniques. In one embodiment of the invention, the serum-derived immunoglobulin concentrate is administered orally. In certain embodiments, the animal plasma, fractions thereof or mixtures thereof according to the invention is administered in a pharmaceutically acceptable aerosol, through a nebulizer or is orally administered (preferably in food).

A "therapeutically effective amount" can be, but is not limited, to an amount of plasma protein composition that is sufficient to provide an improvement in the subject's results in one or more cognitive impairment tests.

The dosage and number of doses (e.g., single or multiple dose) administered to the subject will vary depending upon a variety of factors, including the route of administration, patient conditions and characteristics (sex, age, body weight, health, size), extent of symptoms, concurrent treatments, frequency of treatment and the effect desired, and the like. These parameters can be determined for each system by well-established procedures and analyses, e.g., in phase I, II, and III clinical trials. In one embodiment of the invention, plasma protein composition is administered once daily. In another embodiment of the invention, plasma protein composition is administered twice daily. In another embodiment of the invention, plasma protein composition is administered three times a day. In another embodiment of the invention, plasma protein composition is administered four times daily. In one embodiment of the invention, plasma protein composition is administered from about 1 week to about 25 weeks. In a further embodiment, plasma protein composition is administered from about 1-4 weeks, 1-5 weeks, 1-10 weeks, 1-15 weeks, 1-20 weeks, 5-10 weeks, 5-15 weeks, 5-20 weeks, 5-25 weeks, 10-15 weeks, 10-20 weeks, 10-25 weeks, 15-20 weeks, or 15-25 weeks. In another embodiment of the invention, plasma protein composition is administered for about 1, 2, 3, 4, 5, 6, 7, 8, 9, or 10 months. In another embodiment of the invention, plasma protein composition is administered from about 1-2 months, 1-3 months, 1-4 months, 1-5 months, 1-6 months, 1-7 months, 1-8 months, 1-9 months, 1-10 months, 2-3 months, 2-4 months 2-5 months. In a further embodiment, plasma protein composition is administered for about 1 week. In a further embodiment, plasma protein composition is administered for about 2 weeks. In a further embodiment, SBI is administered for about 3 weeks. In a further embodiment, plasma protein composition is administered for about 4 weeks. In a further embodiment, plasma protein composition is administered for about 24 weeks.

In one embodiment of the invention, plasma protein composition is administered in an amount from about 5 mg to about 100 g to the subject daily. In a further embodiment of the invention, the amount of plasma protein composition administered to the subject daily is from about 10 mg to about 90 g, from about 20 mg to about 80 g, from about 50 mg to about 70 g, from about 100 mg to about 60 g, from about 250 mg to about 50 g, from about 500 mg g to about 50 g. from about 1 g to about 50 g, from about 5 g to about 50 g, or from about 10 g to about 45 g.

In one embodiment of the invention, plasma protein composition is administered in an amount from about 10 mg to about 1 g per kg body weight of the subject per day. In a further embodiment of the invention, the amount of plasma protein composition administered to the subject daily is from about 20 mg to about 900 mg per kg body weight, from about 30 mg to about 800 mg per kg body weight, from about 40 mg to about 750 mg per kg body weight, from about 50 mg to about 700 mg per kg body weight, from about 60 mg to about 650 mg per kg body weight, from about 70 mg to about 600 mg per kg body weight, from about 80 mg to about 550 mg per kg body weight, from about 90 mg to about 500 mg per kg body weight, from about 100 mg to about 500 mg per kg body weight, from about 150 mg to about 450 mg per kg body weight, from about 200 mg to about 400 mg per kg body weight per day.

In certain embodiments, dosages used for a model animal, such as a mouse, rat, dog, or pig, can be converted to an appropriate dose for a human subject using conversion factors that are well known and readily available to those skilled in the art. See, e.g., "*Guidance for Industry: Estimating the Maximum Safe Starting Dose in Initial Clinical Trials for Therapeutics in Adult Healthy Volunteers*," U.S. Dept. of Health and Human Services, July 2005.

In one embodiment of the invention, plasma protein composition is administered in an amount from about 0.05% to about 5% by weight of the subject's total daily dietary intake. In a further embodiment of the invention, plasma protein composition is administered in an amount from about 0.05% to about 0.1%, from about 0.05% to about 0.2%, from about 0.05% to about 0.5%, from about 0.05% to about 1% from about 0.05% to about 2%, from about 0.1% to about 0.2%, from about 0.1% to about 0.5%, from about 0.1% to about 1% from about 0.1% to about 2% from about 0.1% to about 5%, from about 0.5% to about 1%, from about 0.5% to about 2%, from about 0.5% to about 5%, from about 1% to about 2%, from about 1% to about 5%, or from about 2% to about 5% by weight of the subject's total daily dietary intake. In another embodiment, plasma protein composition is administered in an amount of about 0.05%, 0.1%, 0.2%, 0.5%, 1%, 1.5%, 2%, 2.5%, 3%, 4%, or 5% by weight of the subject's total daily dietary intake. In a further embodiment, the amount of plasma protein composition administered is about 0.2% by weight of the subject's total daily dietary intake. In a further embodiment, the amount of plasma protein composition administered is about 0.4% by weight of the subject' total daily dietary intake.

Having described the invention with reference to particular compositions, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

REFERENCES

All publications cited herein are incorporated herein by reference in their entirety for all purposes.

Bene E R. Sepulveda A M, 2014. Clinical test instrument development to identify and track recovery from concussion. *Semin. Speech Lang.* 35:173-185

Brodaty H. Low L-F, Gibson L, Burns K. 2006. What is the best dementia screening instrument for general practitioners to use?. *Am J Geriatr Psychiatry* 14(5):391-400

Coffey R D, Cromwell G L. 2001. Use of spray-dried animal plasma in diets for weanling pigs. *Pig News Info.* 22:39N-48N.

Gao Y Y, Jiang Z Y, Lin Y C, Zheng C T, Zhou G L, Chen F. 2010. Effects of spray-dried animal plasma on serous and intestinal redox status and cytokines of neonatal pigs. *J. Anim. Sci.* doi:10.2527/jas.2010-2967.

Gisbert E, Skalli A, Campbell J. Solovyev M M, Rodriguez C, Dias J. Polo J. 2015. Spray-dried plasma promotes growth, modulates the activity of antioxidant defenses, and enhances the immune status of gilthead sea bream (*Sparus aurata*) fingerlings. *J. Anim. Sci.* 93:278-286. doi:10.2527/jas2014-7491

Heckler M C T, Tranquilim M V, Svicero D J, Barbosa L, Amorim R M. 2014. Clinical feasibility of cognitive testing in dogs (*Canis lupus familiaris*). *J. Vet. Behavior* 9:6-12

Kiraly M A and Kiraly S J. 2007 Traumatic brain injury and delayed sequelae: a review—traumatic brain injury and mild traumatic brain injury (concussion) are precursors to later-onset brain disorders, including early-onset dementia. *TheScientificWorldJOURNAL* 7, 1768-1776. DOI 10.1100/tsw.2007.269.

Maijó M. Miró L, Polo J, Campbell J. Russell L, Crenshaw J, Weaver E, Moretó M, Pérez-Bosque A. 2011. Dietary plasma proteins attenuate the innate immunity response in a mouse model of acute lung injury. *Br J. Nutr*. doi: 10.1017/S0007114511003655.

Maijó M, Miró L, Polo J, Campbell J, Russell L, Crenshaw J. Weaver E, Moretó M, Pérez-Bosque A. 2012. Dietary plasma proteins modulate the adaptive immune response in mice with acute lung inflammation. *JNutr.* 142: 264-70.

Moretó M, Pérez-Bosque A. 2009. Dietary plasma proteins, the intestinal immune system, and the barrier functions of the intestinal mucosa. *J. Anim. Sci.* 87:E92-E100.

Peace R M, Campbell J, Polo J, Crenshaw J. Russell L, Moeser A. 2011. Spray-dried porcine plasma influences intestinal barrier function, inflammation and diarrhea in weaned pigs. *J Nutr.* 141:1312-1317.

Petschow B W, Burnett B, Shaw A L, Weaver E M, Klein G L. 2014. Serum-derived bovine immunoglobulin/protein isolate: postulated mechanism of action for management of enteropathy. *Clin Exp Gastroenterol* 7:181-190 [PMID: 24904221 doi: 10.2147/CEG.S628231].

Shively S, Scher A I, Perl D P, Diaz-Arrastia R. 2012. Dementia resulting from traumatic brain injury: what is the pathology? *Arch. Neurol.* 69(10):1245-1251. doi: 10.1001/archneurol.2011.3747.

Torrallardona D. 2010. Spray-dried animal plasma as an alternative to antibiotics in weanling pigs: a review. *Asian-Aust. J. Anim. Sci.* 32:131-148.

Van Dijk A J, Everts H, Nabuurs M J A, Margry R J C F, Beynen A C. 2001. Growth performance of weanling pigs fed spray-dried animal plasma: a review. *Livest. Prod. Sci.* 68:263-274.

WHO (World Health Organization). Fact sheet 2016. http://www.who.int/mediacentre/factsheets/fs362/en/ Accessed 24 Apr. 2017.

Xiong Y. Mahmood A, Chopp M. 2013. Animal models of traumatic brain injury. *Nature reviews Neuroscience.* 14(2):128-142. doi:10.1038/nrn3407.

EXAMPLES

To study the effect of the administration of animal plasma proteins on cognitive impairment disorders, the inventors used the SAMP8 mouse model of dementia. The SAMP8 mouse model is a group of related inbred strains consisting of senescence-prone inbred strain (SAMP8) and senescence-resistant inbred strain (SAMR1), which have been successfully developed by genetic selection. The characteristic feature of aging common to the SAMP8 and SAMR1 is accelerated senescence and normal aging, respectively.

To that end, SAMP8 mice can be used as a model for dementia in humans and other animals as these mice show age-related behavioral deterioration, such as deficits in learning and memory, emotional disorders (reduced anxiety-like behavior and depressive behavior) and altered circadian rhythm associated. SAMP8 mice have severely impaired acquisition and retention of the passive avoidance response and show impairment in spatial memory tasks, in which the mice learn by escaping from the aversive situation. Brains of SAMP8 mice show similar neuropathological changes to those of Alzheimer's disease brains from humans, that is, deposition of β-amyloid protein. Also SAMP8 mice have spongiform degeneration related with vacuoles of various sizes in the brain while no vacuoles were evident in the brain of SAMR1 mice.

The inventors unexpectedly observed that supplement based on animal plasma proteins, fractions thereof, or mixtures of plasma proteins and fractions thereof fed to SAMP8 mice reduced the nocturnal motor activity of the SAMP8 mice, making the results closer to the pattern shown by the Control-SAMR1 mice, indicating improvements in orientation of these aged animals with markers of cognitive impairment disorders. The inventors also observed that variables of both short-term and long-term memory were deteriorated in aged (6 month-old) mice as compared with younger (2 month-old). The older mice showed lower explorative behaviors and memory retention. Feeding SDP for 4 months reduced the effects of aging on memory indicators, suggesting that SDP might delay the progressive deterioration of cognitive functions. The test used, novel object recognition (NOR) test, is a "pure" recognition memory test and a valid task to assess working memory. The test does not involve positive or negative reinforces and this makes NOR comparable to memory tests currently used in humans. In summary, the inventors surprisingly found that administration of plasma proteins prevents the deterioration of cognitive functions associated with aging.

Example 1—Effects of Plasma Protein Administration on Nocturnal Motor Activity in SAMP8 Mice Materials and Methods:
Animals:
Experiments have been done using a senescence-accelerated prone strain of mice (SAMP8). At 9 months of age, these animals have fully developed senescence. Mice of the senescence resistant strain (SAMR1) were used as controls. Mice were maintained in conventional housing (3-4 animals per cage) for 5 months (except if they showed an aggressive behavior in which case they were separated and housed individually). Mice were monitored for food intake and body weight throughout the experimental period.

Diets:
Mice were fed with the experimental diets for up to 4 months. The composition of experimental diets is detailed in Table 1. Food intake and body weight were monitored throughout the experimental period.

TABLE 1

Composition of experimental diets.
Diets were produced by APC-Europe, S. A.

| Ingredient (g/kg) | Control | SDP |
|---|---|---|
| SDP | — | 80 |
| Corn starch | 199.3 | 335.7 |
| Skim milk | 530.7 | 370.1 |
| Sucrose | 94.5 | 102.7 |
| Soybean oil | 70 | 76.1 |
| Cellulose | 50 | 54.4 |

TABLE 1-continued

Composition of experimental diets.
Diets were produced by APC-Europe, S. A.

| Ingredient (g/kg) | Control | SDP |
|---|---|---|
| AIN-93-G-MX (94046)* | 35 | 38 |
| AIN-93 VX (94047)* | 15 | 16.3 |
| DL-Methionine | 2.5 | 3.5 |
| Choline bitartrate | 3 | 3.3 |

In this study, the average mouse weight was 32 g and the average daily feed intake was 4.5 g. This provided an average daily plasma intake of 11.25 g SDP/kg body weight. Based on composition of plasma being approximately 20% IgG, the average daily IgG intake was 2.25 g IgG/kg body weight.

Experimental Design:

Animals received the experimental diet for 3 months (from 6 to 9 months of age). The 6 month-old animals were distributed into three groups: SAMR1 (SAMR1 mice fed the Control diet), SAMP8 (SAMP8 mice fed the Control diet), and SAMP8-SDP (SAMP8 mice fed the SDP-supplemented diet). Body weight was recorded weekly. Animals were sacrificed when were 9 month-old and samples were taken.

To study the effects of the different strains and the effects of dietary supplementation, data were analyzed by one-way ANOVA followed by the Bonferroni post hoc test, using SPSS-20.0 software (SPSS Inc., Chicago, Ill.). In both analyses, differences were considered significant at $P<0.05$.

Motor Activity:

Five days before sacrifice, animals were housed individually

Pattern of motor activity was studied for five days under a 12-12 hours light (LL)-dark (DD) cycle Behavioral Analysis:

Motor activity was recorded through activity meters

Registration of the times that the mouse crosses one of the infrared beams

Data recorded every 15 minutes

Calculations done with an integrated package for chronobiology

Results:

Body Weight Evolution:

The body weight of the SAMP8 population was about a 10% lower than the SAMPR1 mice during the period studied, starting at week 26 (6 months-old) until week 39 (9 months-old; $P<0.05$; FIG. 1). Supplementation with SDP did not modify this pattern. Results are expressed as means±SEM (n=20-30 mice). * Indicates differences between SAMR1 and SAMP8. $P<0.05$.

Figure 2:
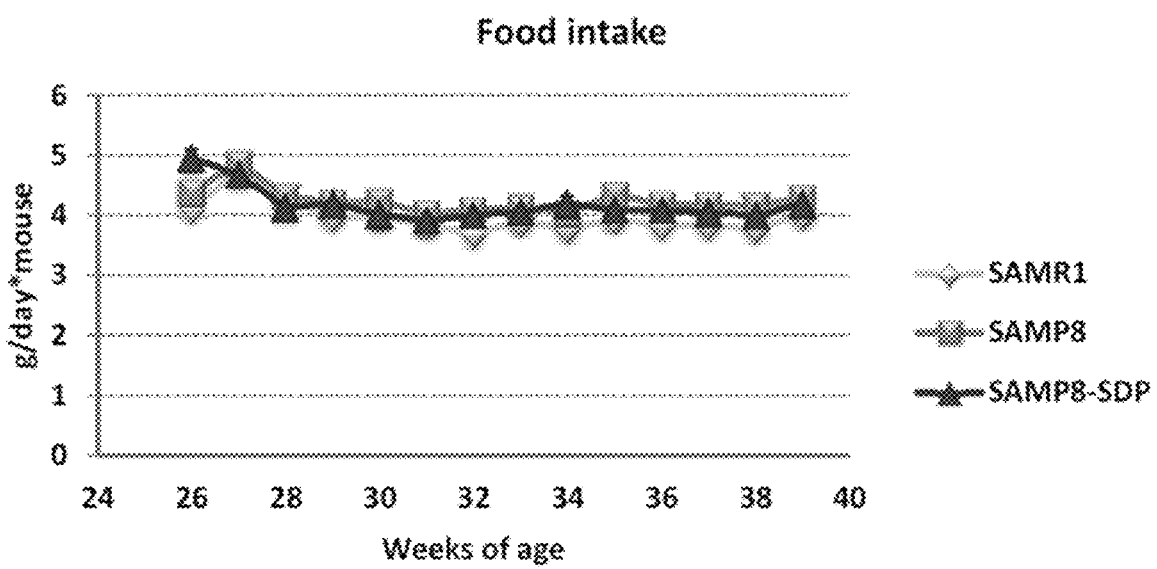
FIG. 2 provides the food intake of control and experimental mice. Results are expressed as means±SEM (n=20-30 mice).

Food Consumption:

Food intake was measured three times per week during the feeding period. FIG. 2 summarizes the daily mean food consumption. Food intake was the same in all groups.

Figure 3:
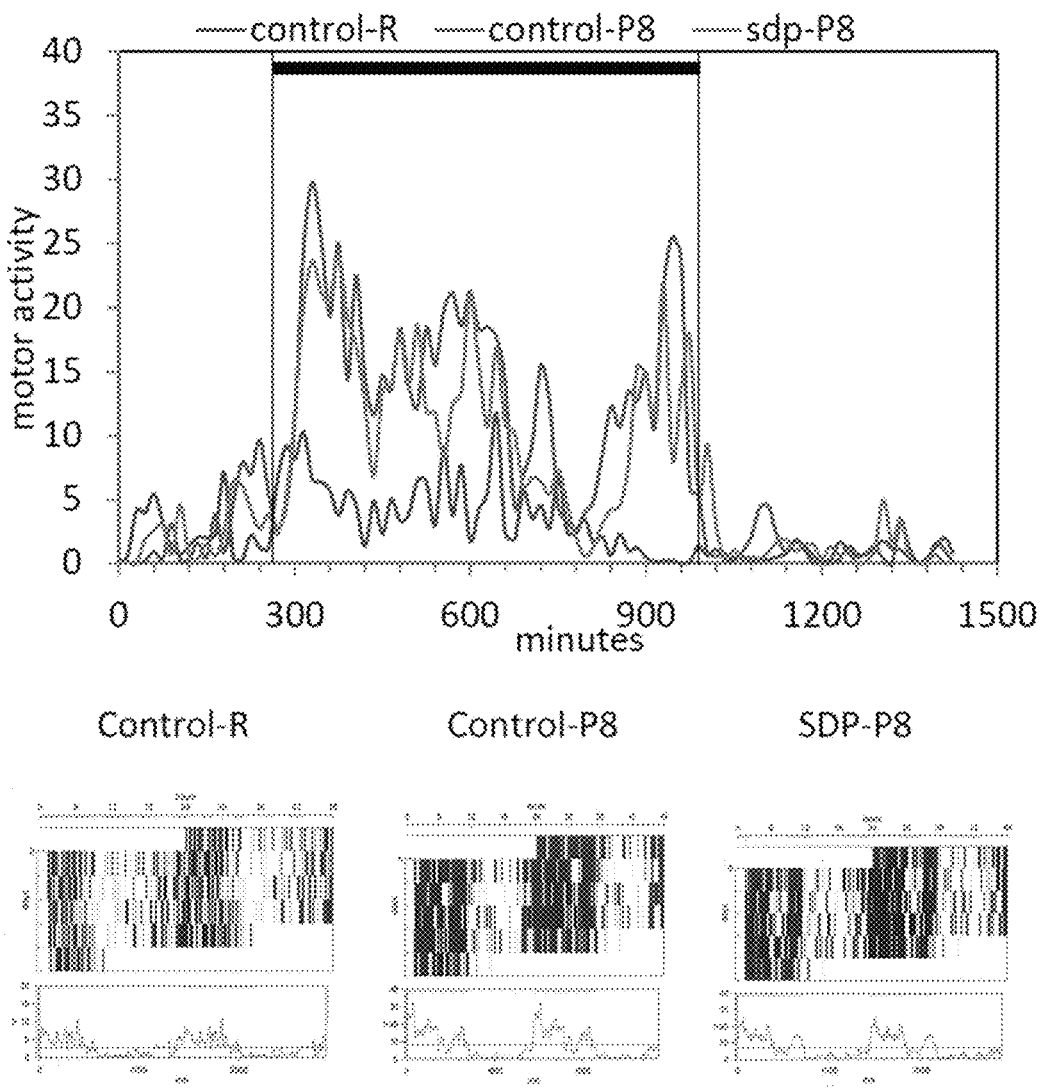
FIG. 3 provides a motor activity dendrogram.

Motor Activity:

The SAMP8 strain shows a higher nocturnal motor activity than the SAMR1 strain (FIG. 3). This would indicate that the aging pattern of this animal model is associated with increased nocturnal motor activity.

The control SAMP8 mice show larger nocturnal activity than resistant mice (Control-SAMR1), indicating that there are basal activity level differences between both strains. This higher increase on motor activity in SAMP8 strains can be related with the fact that these animals had reduced memory and learning capacity, therefore these animals may have had lower orientation, as is typical in Alzheimer's disease, which can explain the higher activity of this strain compared with the resistant SAMR1 strain.

Analysis of the DD/LL ratios support the view that SDP fed animals have an intermediate pattern between the values observed by the Control-SAMR1 group and the Control-SAMP8 group. The results indicated that SAMP8 mice fed with SDP supplementation had reduced dark activity compared with SAMP8 mice fed control feed. This may indicate that supplementation with SDP helps to improve orientation and memory of these animals and reduce negative effects associated with dementia.

Conclusions:

Results from motor activity analysis, though preliminary, suggest that SDP supplementation reduced the nocturnal motor activity of the SAMP8 mice making it closer to the pattern shown by the Control-SAMR1 mice. This suggests that administration of the animal plasma, fractions thereof, or mixtures thereof can be used in treating cognitive impairment disorders, such as dementia.

Example 2—Effects of Plasma Protein Administration on Learning and Memory Functions in SAMP8 Mice Materials and Methods:

Animals:

Experiments have been done using SAMP8 mice. Mice were maintained in conventional housing (3-4 animals per cage) until the age of 2 months (except if they showed an aggressive behavior in which case they were separated and housed individually).

Diets:

Mice were fed with the experimental diets for up to 4 months. The composition of experimental diets is detailed in Table 1 of Example 1. Food intake and body weight were monitored throughout the experimental period.

Figure 4:
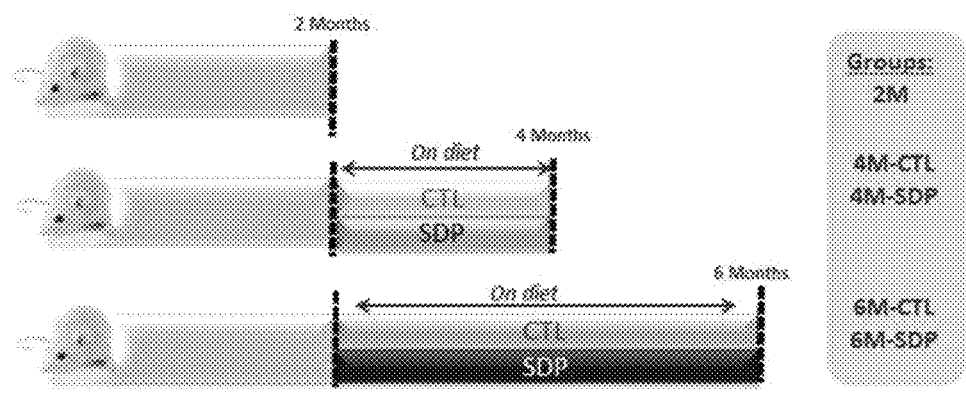
FIG. 4 provides the experimental design and groups used to study the cognitive function.

Experimental Design:

In this set of the experiments, the inventors aimed to know the effect of plasma protein administration on short and long-term memory in SAMP8 mice by performing the Novel Object Recognition (NOR) Test. The following experimental groups were used (FIG. 4):

2M: mice of 2-month-old, young reference group.

4M-CTL: mice of 4-month-old, fed with control diet for 2 months.

4M-SDP: mice of 4-month-old, fed with SDP supplemented diet for 2 months.

6M-CTL: mice of 6-month-old (senescent), fed with control diet for 4 months.

6M-SDP: mice of 6-month-old (senescent), fed with SDP supplemented diet for 4 months.

Food intake and evolution of the body weight were evaluated from 2 to 6 months of age. To study the effect of aging and the effect of dietary supplementation, data were analyzed by one-way analysis of variance (ANOVA) followed by the Fisher post hoc test using the GraphPad Prism® software ver. 6 (GraphPad Software, Inc., USA). Body weight has been analyzed by two-way ANOVA followed by the Fisher post hoc test. Differences were considered significant at $P<0.1$.

Figure 5:
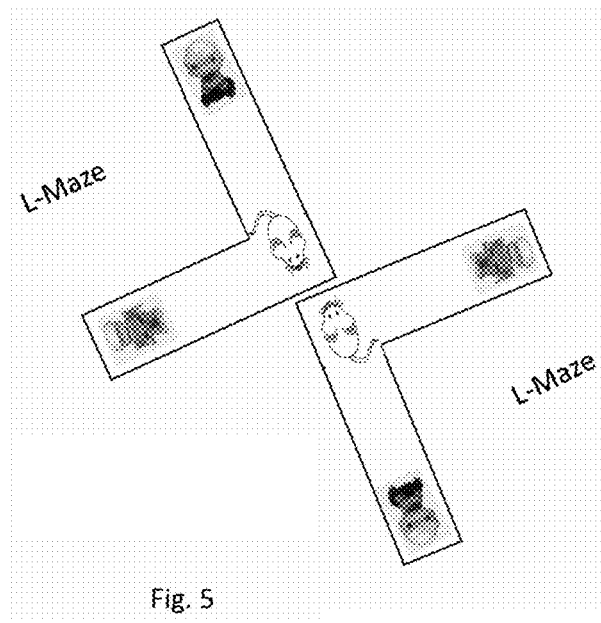
FIG. 5 provides an image of an NOR Test maze.

Novel Object Recognition Test (NORT):

Mice were placed in a 90°, two-arm (25-cm-long, 20-cm-high, 5-cm-wide) black maze (FIG. 5). Light intensity in the middle of the maze was 30 lx. The objects to be discriminated were made of plastic. Mice (one at a time) were individually put in the maze for 10 min during three consecutive days. On the fourth day, animals were submitted to a 10 min acquisition trial, in which they were placed in the maze in the presence of two identical objects (A+A or B+B) situated at the end of each arm. During this trial, the explorative preference (the percentage of time exploring each object) and the explorative index (defined as the time exploring both objects/time on the maze) were measured. A 10 min retention trial was carried out 2 h later that evaluates the short-time memory. During this trial, one of the objects was replaced by a novel one (A+B or B+A) and the behavior of the mice was recorded with a camera. The time spent exploring the novel object (TN) and the time exploring the old object (TO) were measured. The discrimination index (DI) was calculated by (TN−TO)/(TN+TO). Mice with a DI equal or higher than 0.2 have been considered as animals "with memory." In order to avoid object preference biases, objects A and B were counterbalanced so that one half of the animals in each experimental group were exposed first to object A and then to object B, whereas the remaining half saw object B first and then object A. The maze and the objects were cleaned with 96% ethanol after each test in order to eliminate olfactory cues. Twenty-four hours later, a second retention trial was performed to evaluate the long-time memory. During this second trial, the formerly novel object was replaced by another one (A+C or B+C) and, again, the behavior of the mice was recorded with a camera and DI was calculated.

Figure 6:
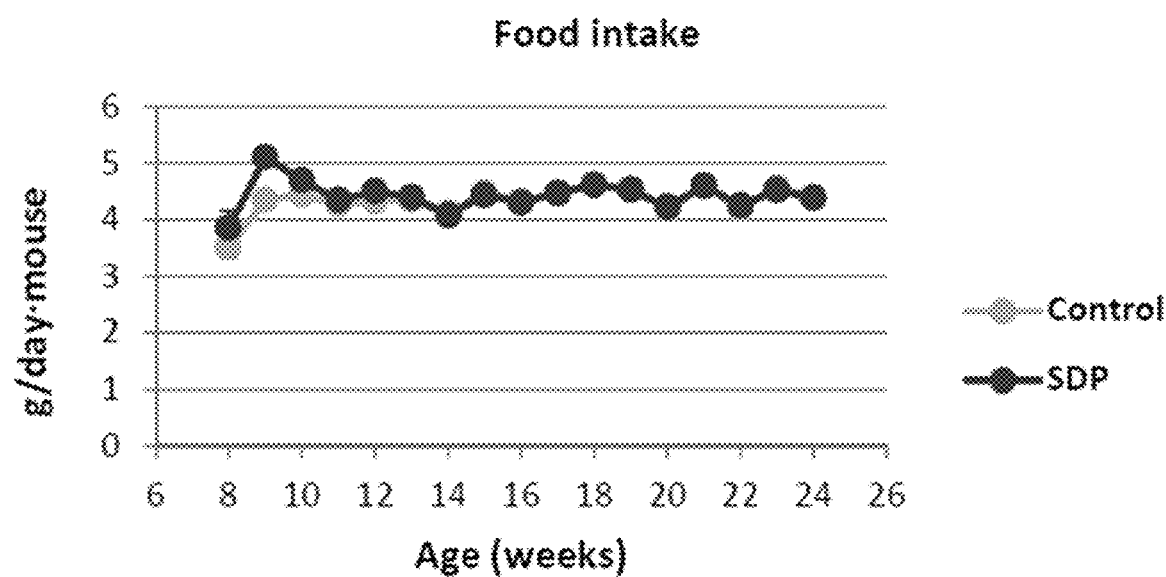
FIG. 6 provides the food intake of control and experimental mice. Results are expressed as means±SEM (n=34-40 mice).

Results:

Food Intake and Body Weight:

Food intake was measured three times per week during the feeding period. FIG. 6 summarizes the daily mean food intake during the 4 months that mice have received the experimental diets. No differences have been observed between mice fed with control and SDP diet.

Figure 7:
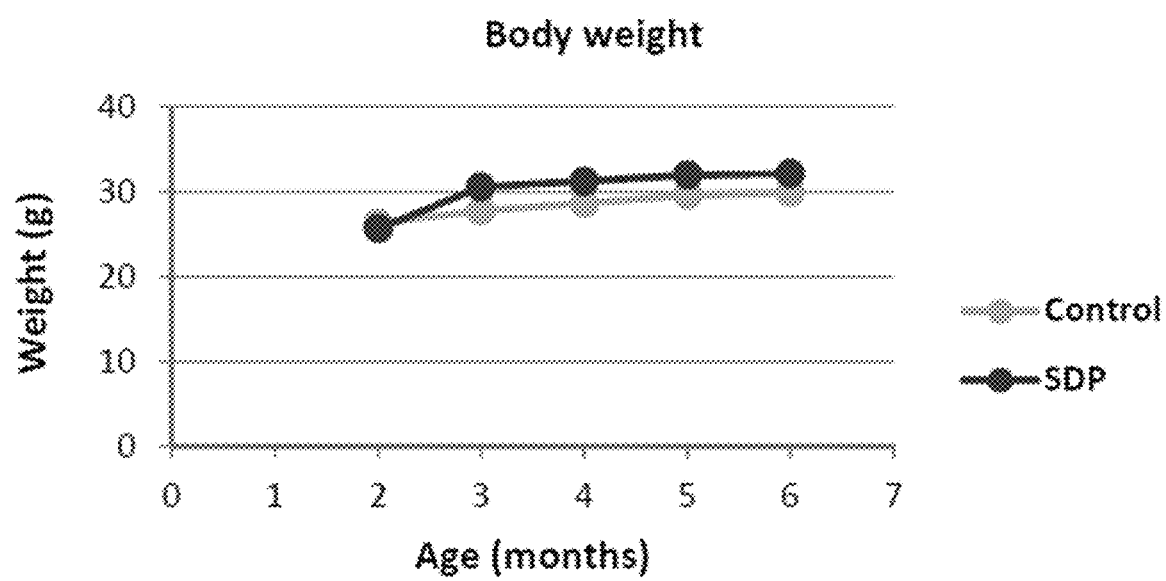
FIG. 7 provides evolution of body weights of SAMP8 mice, with or without SDP supplementation. Results are expressed as means±SEM (n=9-19 mice). Means with a common letter differ, P<0.1.

The body weight of SAMP8 mice was measured once a month. At 2-month-old, SAMP8 mice have a similar body weight. After 1 month feeding with SDP diet, SAMP8 mice have an increased body weight gain than those fed with control diet (FIG. 7), and this difference was maintained along the experimental period.

Figure 8:
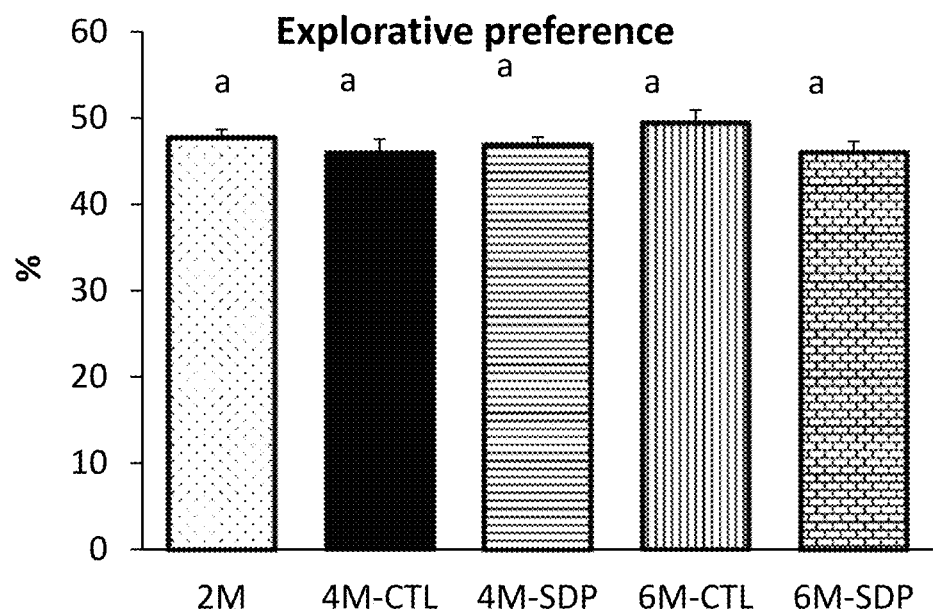
FIG. 8 provides the explorative preference of the experimental groups. Results are expressed as means±SEM (n=10-13 mice).

Novel Object Recognition Test (NORT):

Mice did not show any preference for one of the identical objects during the acquisition trial as shown in FIG. 8, where all the groups presented an explorative preference nearly to 50%. This result indicates that no group preferred one of the arms of the maze.

Figure 9:
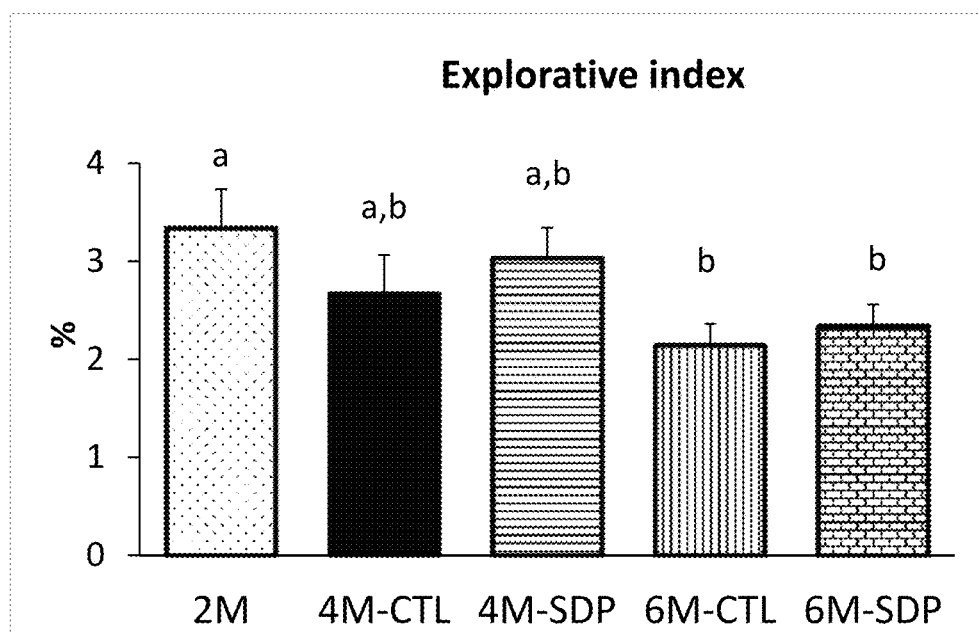
FIG. 9 provides the explorative index at 5 min of the acquisition trial. Results are expressed as means±SEM (n=10-13 mice). Means with a common letter differ, P<0.1.

FIG. 9 shows the explorative index calculated during the first 5 min of the acquisition trial. At 2-month-old, mice explored the objects 3.3±0.4% of the time spent in the maze. In dementia-model mice, this index decreased over time, eventually reaching 2.1±0.4% (P<0.1) at 6 months of age, indicating a lower explorative capacity. Administration of plasma protein compositions does not prevent this effect associated to age.

Figure 10:
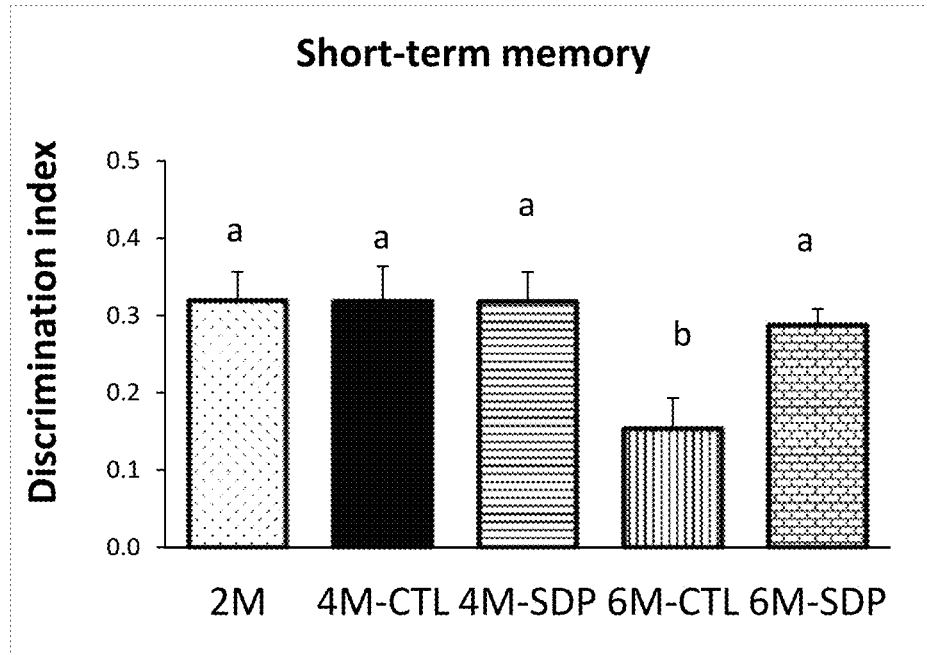
FIG. 10 provides the discrimination index for each of the experimental groups in the first retention trial, which evaluated short-term memory retention. Results are expressed as means±SEM (n=10-13 mice). Means with a common letter differ, P<0.1.
Figure 11:
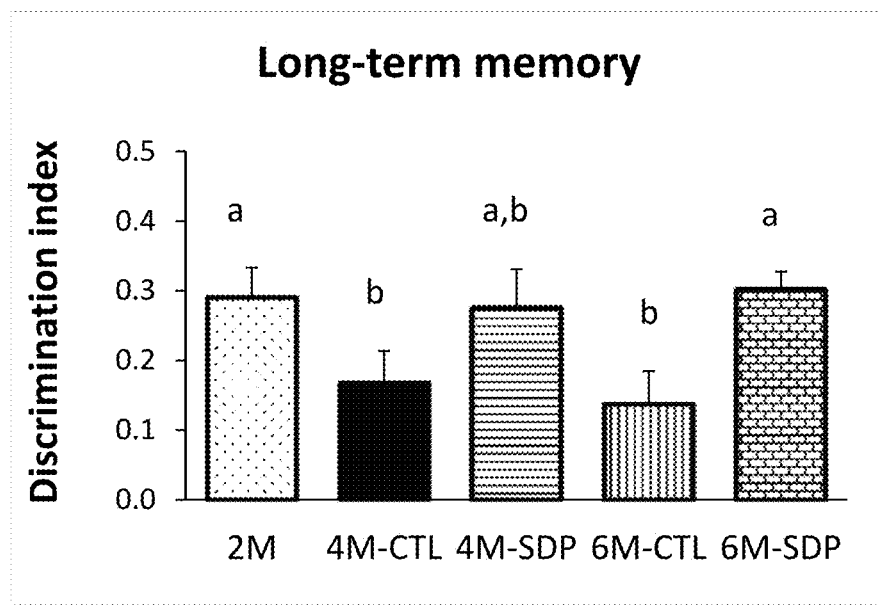
FIG. 11 provides the discrimination index for each of the experimental groups in the second retention trial, which evaluated long-term memory retention. Results are expressed as means±SEM (n=10-13 mice). Means with a common letter differ, P<0.1.

On the first retention trial (evaluates the short-term memory; FIG. 10), the discrimination index decreased at 6-month-old during the first 5 min of the test, indicating a reduction on the short-term memory in the dementia-model mice. However, 6-month-old mice supplemented with SDP diet maintained the same results seen in 2-month-old mice and had a significantly improved discrimination index compared to 6-month-old mice fed the control diet. The same pattern is observed on the second retention trial (24 h after the first retention trial) in dementia-model mice that is associated with the long-term memory (FIG. 11). At 4-month-old, the long-term memory is already significantly impaired in dementia-model mice fed the control diet with a similar level of impairment observed in 6-month-old control animals. Dementia-model mice supplemented with SDP showed an increased discrimination index (suggesting improved long term memory) at 4 months, although not significantly different from control animals. However, at 6 months, dementia-model mice supplemented with SDP showed an increased discrimination index that was statistically greater than 6-month-old SAMP8 mice fed the control diet and similar to the discrimination index observed at 2 months.

Figure 12:
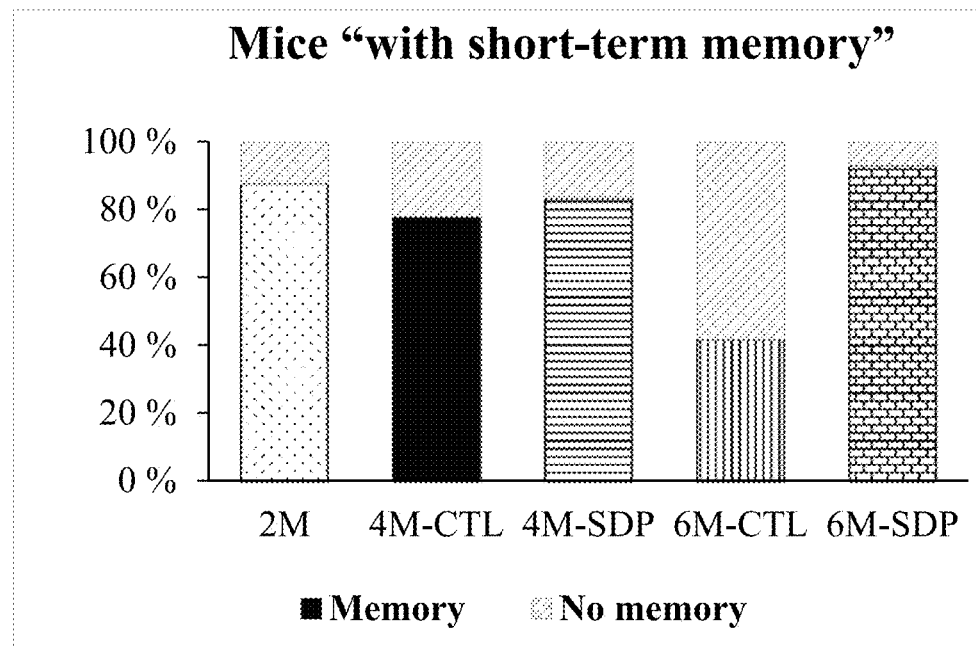
FIG. 12 provides the percentage of mice determined to possess and lack a sufficient short-term memory in each of the experimental groups in the first retention trial (n=10-13 mice).

On FIG. 12 is represented the percentage of mice "with memory," understood as a DI higher than 0.2; during the first retention trial. This value is reached when the mouse spends twice the amount of time exploring the novel object in comparison with the old object. When mice were 2-months-old, nearly 90% of the population conserved the short-term memory, while at 6-months of age, this percentage decreased to about 40% in control mice. However, when mice were administered plasma protein compositions, the percentage of mice "with memory" at 4- and 6-months of age is similar to that found in the younger group.

Figure 13:
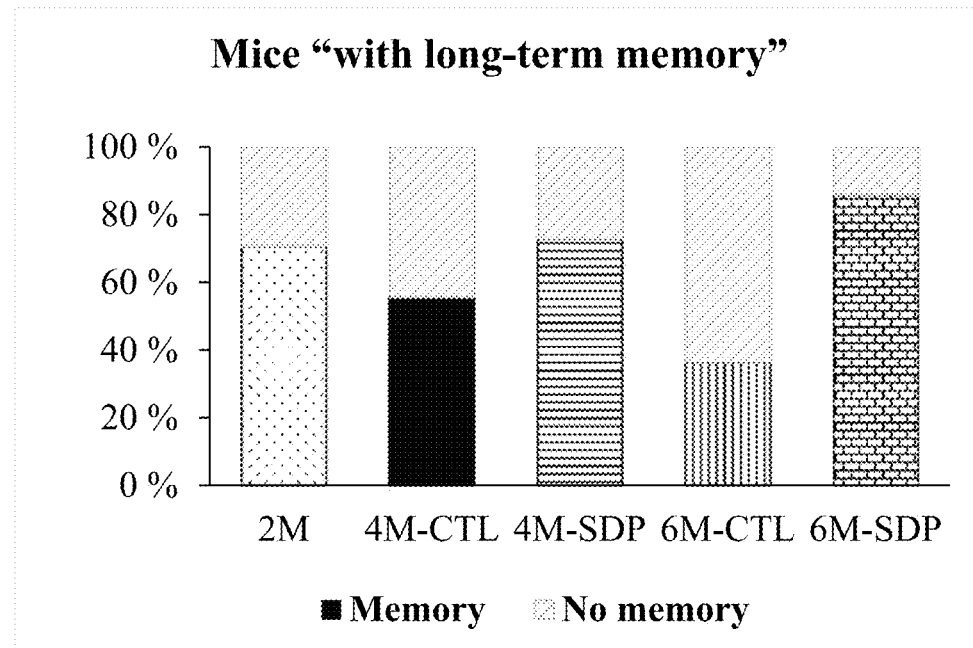
FIG. 13 provides the percentage of mice determined to possess and lack a sufficient long-term memory in each of the experimental groups in the second retention trial (n=10-13 mice).

In the second retention trial, approximately 70% of the 2-month-old mice conserved the long-term memory (FIG. 13). This percentage decreased with age, taking values of 56% for the 4-month-old mice and 36% for the 6-month-old mice. However, when mice were administered plasma protein compositions, the percentage of mice "with long-term memory" at 4- and 6-months of age is similar to, or even better than, that found in the younger group.

Conclusions:

The Novel Object Recognition Test (NORT) evaluates recognition memory and is useful to study short-term and long-term memory. NORT is a "pure" recognition memory test and a valid task to assess working memory. The test does not involve positive or negative reinforces and this makes NOR comparable to memory tests currently used in humans for dementia diseases, such as Alzheimer's disease. Using this test, it was observed that variables of both short-term and long-term memory were deteriorated in aged (6 month-old) mice as compared with younger (2 month-old) mice in the SAMP8 dementia model. The older mice showed lower explorative behaviors and memory retention. Unexpectedly, feeding a diet supplemented with plasma protein compositions (e.g., SDP) for 4 months reduced the severity of memory loss in the dementia model mice, suggesting that this might delay the progressive deterioration of cognitive functions.

In summary, administration of a diet supplemented with plasma protein compositions prevented the deterioration of cognitive functions associated with dementia, as demonstrated by the Novel Object Recognition test.

Example 3—Effects of Plasma Protein Administration on Expression of Synaptophysin, a Neural Function Marker in SAMP8 Mice Aim:

Six-month-old SAMP8 mice show a reduced expression of neural function markers, such as synaptophysin-1, as compared to control mice, suggesting a decrease in the number of synaptic connections in the SAMP8 mice. In this set of experiments the inventors aimed to determine whether SDP supplementation for 4 months could prevent the reduction in the synaptophysin-1 neural function markers, thereby suggesting a reduction in neural degeneration in 6-month-old SAMP8 mice.

Materials and Methods:

Animals:

Experiments were again performed using a senescence-accelerated prone strain of mice (SAMP8), AND THE MICE FROM Example 2 were used for this experiment, as well. The experimental groups employed were:

2M: mice of 2-month-old, young reference group;

6M-CTL: mice of 6-month-old (senescent), fed with control diet for 4 months; and 6M-SDP: mice of 6-month-old (senescent), fed with SDP supplemented diet for 4 months.

Sample Collection and Homogenization:

At the end of the experiment of example 2, mice were anaesthetized with xilacin/ketamine. The brain was removed and samples of cortex and hippocampus were quickly frozen at −80° C. for further uses. Samples of cortex and hippocampus were homogenized with a Polytron (PRO Scientific Inc. USA) at 20,000 rpm in a lysis buffer containing 50 mM Tris-HCl, 150 mM NaCl, 2 mM EDTA, 1% Triton, 200 mM PMSF, 1 mM DTT and 2% (v/v) inhibitor protease cocktail. The homogenate was centrifuged at 4° C. at 955 g for 20 min.

Determining Protein Abundance by Western Blot:

Samples (50 μg of protein from cortex and hippocampus) were denatured and separated on 10-12.5% SDS-PAGE polyacrylamide gels and transferred to polyvinylidene difluoride membranes. Membranes were blocked by incubation for 90 min at room temperature in Tris buffered saline containing 0.1% Tween 20 (TBST) and 5% dry milk, and then incubated overnight with a mouse anti-synaptophysin (obtained from Dako) (1/3000 dilution) at 4° C. Membranes were washed several times with TBST and incubated for 2 h with an anti-mouse horseradish peroxidase-conjugated secondary antibody (Sigma-Aldrich, USA). After washing with TBST, protein bands were visualized using the Clarity chemiluminescence detection kit (Bio-Rad, USA). The assay was carried out in accordance with the manufacturer's instructions. After their detection, bands were quantified using ImageLab (Bio-Rad).

Statistical Analysis:

Data were analyzed by one-way analysis of variance (ANOVA) followed by the Fisher post hoc test using the GraphPad Prism® software ver. 6 (GraphPad Software, Inc., USA). Protein abundance has been analyzed by two-way ANOVA followed by the Fisher post hoc test. Differences were considered significant at P<0.1.

Figure 14:
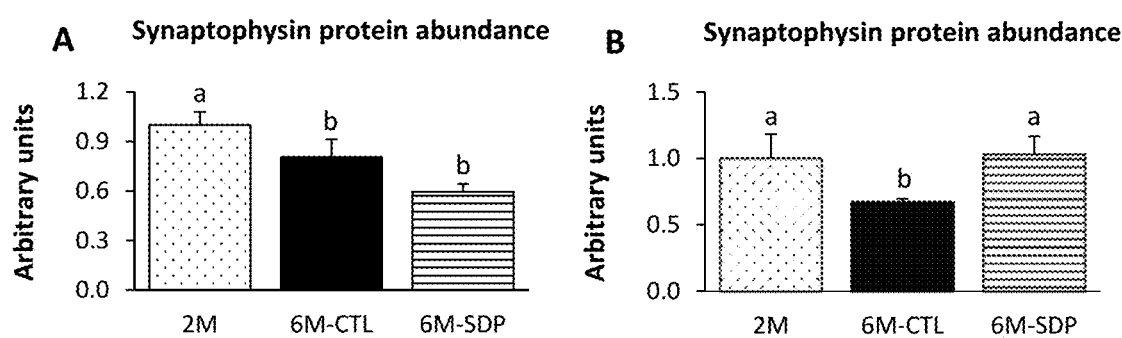
FIG. 14 provides the expression of synaptophysin in cortex (panel A) and in hippocampus (panel B) for mice in the 2-month, 6-month control, and 6-month SDP groups. Results are expressed as means±SEM (n=6-8 mice). Means with a common letter differ, P<0.01.

Results:

FIG. 14 shows the expression of the synaptophysin, which is a protein involved in the neuronal synapsis. The abundance of this protein was reduced in the cortex and hippocampus of aged mice with markers of cognitive impairment disorders (P<0.05 and P=0.053, respectively; FIGS. 14A and 14B, respectively). SDP supplemented diet showed different effects regarding brain tissue, since there was no dietary effect on cortex, but SDP prevented aged-associated reduction in synaptophysin in hippocampus (P<0.05). Therefore, the animal plasma, fractions thereof, or mixtures thereof according to the invention is effective in treating the reduced expression of synaptophysin protein in the hippocampus in senescent animals.

Example 4—Effects of Plasma Protein Administration on Expression of Markers Associated with Microgliosis, Astrogliosis and Amyloid Plaque Formation in SAMP8 Mice Aim:

In this set of experiments, the inventors aimed to determine whether SDP supplementation for 4 months could affect microgliosis and astrogliosis associated to senescence, as well as amyloid plaques formation.

Altered synaptic morphology, progressive loss of synapses and glial (astrocyte and microglial) cell activation are considered as characteristic hallmarks of certain cognitive dysfunction disorders, including those associated with aging. Neuronal loss during senescence decreases the expression of the presynaptic protein synaptophysin and the post-synaptic protein PSD-95. Thus, analysis of synaptophysin and PSD-95 in brain tissue provides information about neuronal integrity.

Emerging evidence implies that glial dysregulation may have a significant impact on the disease onset of AD. Reactive astrogliosis is a universally acknowledged feature of AD. Moreover, the degree of astrogliosis is correlated with cognitive decline (Frost and Li, 2017). Microglial cells are able to undergo directed changes in immunophenotype in regulating the functions of various brain structures and in the process of development of age-related and mental pathology. Thus, analysis of GFAP and IBA1 in brain tissue provide information about the microgliosis and astrogliosis in senescent mice. β-amyloid plaques and tau hyperphosphorylation have been considered the principal mechanisms associated with the development of AD. Quantification of Tau, p-Tau and amyloid precursor protein in brain tissue provide information about principal markers of AD in brain tissue of senescent mice.

Materials and Methods:

Animals:

Experiments were again performed using a senescence-accelerated prone strain of mice (SAMP8), which were taken and grown in the animal facility of the Facultat de Farmácia i Ciéncies de l'Alimentació of the Universitat de Barcelona (UB). Protocols used in this example were approved by the Animal Experimentation Ethics Committee (CEEA) of the UB, in accordance with the Generalitat de Catalunya's guidelines for the Care and Use of Laboratory Animals (DAAM: 7939 and 9272).

Diets:

Mice were fed with the experimental diets for 2 or 4 months. The composition of experimental diets is detailed in Table 2.

TABLE 2

Composition of experimental diets. SDP was provided by APC-Europe, S. A.. AIN-93 VX is a vitamin mix and AIN-93-G-MX is a mineral mix, both of which were provided by Envigo, Italy.

| Ingredient (g/kg) | Control | SDP |
|---|---|---|
| SDP | — | 80 |
| Corn starch | 199.3 | 308.8 |
| Skim milk | 530.7 | 340.5 |
| Sucrose | 94.5 | 94.5 |
| Soybean oil | 70 | 70 |
| Cellulose | 50 | 50 |
| AIN-93-G-MX (94046)[2] | 35 | 35 |
| AIN-93 VX (94047)[2] | 15 | 15 |

TABLE 2-continued

Composition of experimental diets. SDP was provided by APC-Europe, S. A.. AIN-93 VX is a vitamin mix and AIN-93-G-MX is a mineral mix, both of which were provided by Envigo, Italy.

| Ingredient (g/kg) | Control | SDP |
|---|---|---|
| Choline bitartrate | 3 | 3 |
| DL-Methionine | 2.5 | 3.2 |

Experimental Design:

Mice were maintained in conventional housing (3-4 animals per cage) until the age of 2 months feeding the commercial standard feed. After 2 months, the animals were fed experimental diets (Control or SDP) for 4 months. The experimental design of this study consisted in 3 groups of 9-11 animals/group:

2M: mice of 2-months-old, young reference group;

6M-CTL: mice of 6-months-old, fed with Control diet for 4 months; and

6M-SDP: mice of 6-months-old, fed with SDP supplemented diet for 4 months.

Sample Collection:

At the end of the experiment, mice were anaesthetized with xilacin/ketamine. Blood was directly collected from the heart and then killed by exsanguination. The brain was removed and was quickly frozen at −80° C. for further uses.

Perfusion Mice:

Mice were anaesthetized and transcardially perfused thoroughly with PBS to remove all of the intravascularly distributed dye. Afterwards, mice were perfused with 4% paraformaldehyde. The brain was removed and samples of hemispheres were quickly frozen at −80° C. for further uses.

Sample Homogenization:

Samples of brain hemisphere were homogenized with a Polytron (PRO Scientific Inc, USA) at 20,000 rpm in a lysis buffer containing 50 mM Tris-HCl, 150 mM NaCl, 2 mM EDTA, 1% Triton, 1 mM PMSF, 1 mM DTT and 2% (v/v) inhibitor protease cocktail. The homogenate was centrifuged at 4° C. at 955 g for 20 min.

Immunohistochemistry:

Perfuse brains were embedded in a drop of Tissue-Tek O.C.T. Compound (Miles) and immediately submerged into isopentane. They were then stored at −80° C. Brains were cut with a cryostat CM3050S (Leica Microsystems). Brain sections were permeabilized with a solution containing 10 g/L bovine serum albumin, glycine 20 mM (both, Sigma-Aldrich-Aldrich, USA) and Triton X-100 1% (v:v; Fluka. USA) in PBS at room temperature for 30 min. The slices were incubated overnight at 4° C. with a solution containing 10 giL bovine serum albumin, glycine 20 mM and the corresponding primary mouse monoclonal antibody in a humidified chamber. The primary antibodies used were Iba-1 (Wako Chemicals, USA), GFAP (Abcam, United Kingdom), NeuN and CD11b (Millipore, USA). Sections were washed with PBS and incubated with Alexa Fluor secondary antibody for 2 h at room temperature in a humidity chamber. Afterwards, the samples were washed in PBS and counterstained with nuclear marker Hoechst 33258 (Calbiochem, USA) for 20 min at room temperature. They were then washed again with PBS and mounted in Mowiol-488 (Calbiochem. USA). Negative controls were performed without the primary antibodies. The samples were stored at 4 C until observation by confocal microscopy.

Confocal Scanning Laser Microscope and Image Processing:

Digital fluorescence images were acquired by confocal scanning laser microscope SPII (Leica Microsystems) (images not shown). Five different fields for each cellular staining were analyzed in a blinded fashion, resulting in a minimum of 25 images per animal. Images were analyzed using Fiji (Schindelin et al., 2012). Results expressed as percentage positive cells of total cells/field.

Western Blot:

Western blot procedures were performed according to a previous study (Pérez-Bosque et al., 2016). Samples of brain hemisphere were homogenized and protein concentration was determined using the Bradford method (Bio-Rad, Hercules, Calif., USA). Equal amounts of protein (100 µg) were separated on 10-18% SDS-PAGE and transferred to polyvinylidene difluoride membranes (Bio-Rad, Hercules, USA). Membranes were blocked by incubation for 90 min at room temperature in Tris buffered saline containing 0.1% Tween 20 (TBST) and 5% dry milk. Afterwards, membranes were incubated overnight at 4° C. with diluted primary antibodies Table 2. Membranes were washed and incubated with HRP-conjugated secondary antibodies (Sigma-Aldrich, St Louis, Mich., USA) for 2 h at room temperature. Protein bands were visualized using a chemiluminescence detection kit Clarity and ChemiDoc XRS+ instrument (both from Bio-Rad, Hercules, Calif., USA). After their detection, hybridization bands were quantified using ImageJ gel analyzer software.

TABLE 3

List of antibodies used for Western Blot.

| Antibody | Host | Dilution | Source |
|---|---|---|---|
| NeuN | Mouse | 1/750 | Millipore |
| p-Tau | Mouse | 1/1000 | Invitrogen |
| PSD-95 | Mouse | 1/1000 | Abcam |
| sAPPα | Rabbit | 1/1000 | Covance |
| sAPPβ | Rabbit | 1/1000 | Covance |
| Synaptophysin | Mouse | 1/3000 | Dako |
| Tau | Mouse | 1/1000 | Millipore |
| β-actin | Mouse | 1/30000 | Sigma-Aldrich |

Real-Time PCR:

RNA extraction and reverse transcription were carried out as described previously (Pérez-Bosque et al., 2016). RNA quality and quantity were assessed by spectrophotometry (NanoDrop ND-1000; ThermoFisher Scientific, Waltham, Mass., USA). Total RNA was reverse-transcribed using iScript™ cDNA Synthesis Kit (Bio-Rad, Hercules, Calif., USA). Real-time PCR was performed on a MiniOpticon Real-Time PCR System (Bio-Rad, Hercules, Calif., USA). TaqMan gene expression assays (Applied Biosystems, N.Y., USA) were used for the following genes: β-secretase (Bace1, Mm00478664_ml) and Disintegrin and Metalloproteinase 10 (Adam10, Mm00545742_ml) following the manufacturer's instruction. Each PCR run included duplicates of reverse transcription for each sample and negative controls (reverse transcription-free samples, RNA-free sample). Quantification of the target gene transcripts was done using hypoxanthine phosphoribosyltransferase 1 (Hprt1, Mm00446968_ml) gene expression as reference, and was carried out with the 2-ΔΔCT method (Schmittgen & Livak, 2008). Product fidelity was confirmed by melt-curve analysis.

Statistical Analysis:

Results are expressed as means±standard error of the mean (SEM). To study the effects of aging and the dietary supplementation, data were analyzed by one-way analysis of variance (ANOVA) followed by the Fisher post hoc test using the GraphPad Prism® software ver. 6 (GraphPad Software, Inc., USA). Differences in tests were considered statistically significant when P<0.05. A value of P between 0.05 and 0.1 was considered to establish a significant trend (Curran-Everett & Benos, 2004).

Figure 15:
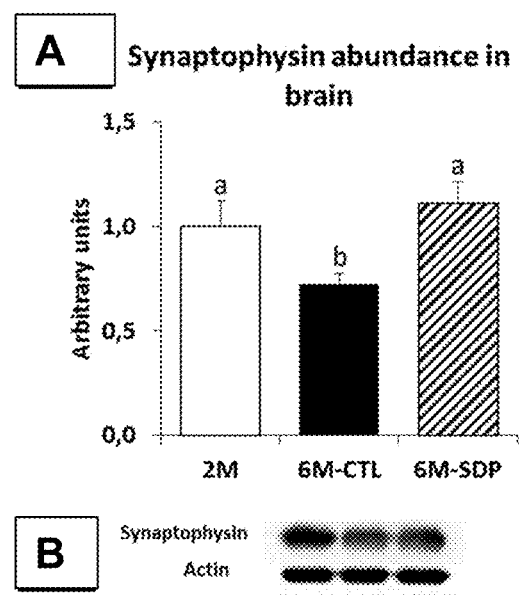
FIG. 15 provides the expression (Real-Time PCR) and abundance (Western Blot) of synaptophysis in brain tissue.

Results:

FIG. 15 shows the expression and abundance in brain tissue of synaptophysin, which is a major integral membrane glycoprotein in presynaptic vesicles of neurons. Results are expressed as means±SEM (n=6-7 mice). FIG. 15A shows the results of Real-Time PCR. Means without a common letter differ, P<0.1. FIG. 15B shows representative images of the Western Blot of synaptophysin and D-actin (control). The abundance of synaptophysin decreased in senescent mice and SDP supplementation preserves the neuronal integrity in older mice.

Figure 16:
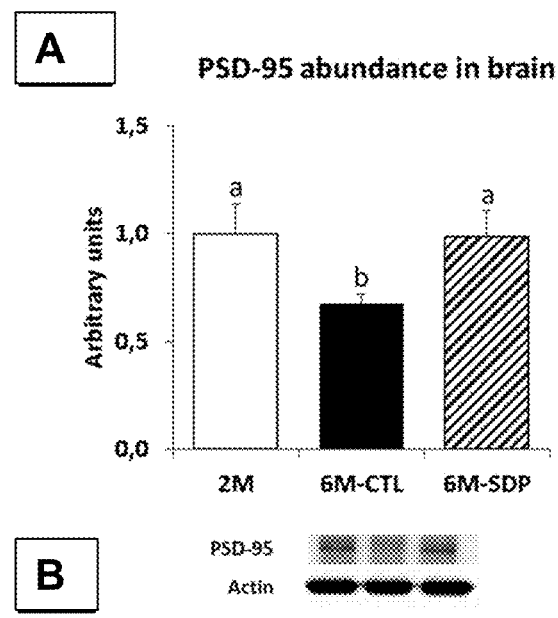
FIG. 16 provides the expression (Real-Time PCR) and abundance (Western Blot) of PSD-95 in brain tissue.

FIG. 16 shows the expression and abundance in brain tissue of PSD-95, which has an important role in the molecular organization of the postsynaptic density. Results are expressed as means±SEM (n=6-7 mice). FIG. 16A shows the results of Real-Time PCR. Means without a common letter differ, P<0.1. FIG. 16B shows representative images of the Western Blot of PSD-95 and β-actin (control). The abundance of PSD-95 decreased in senescent mice and SDP supplementation preserves the neuronal integrity in older mice.

Figure 17:
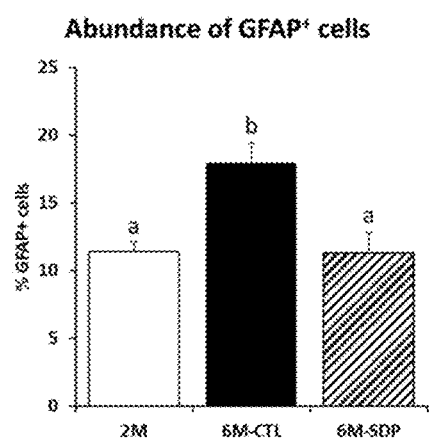
FIG. 17 provides the abundance (immunohistochemistry) of GFAP in brain cells.

FIG. 17 shows the abundance in brain tissue of Glial fibrillary acidic protein (GFAP), which is the main intermediate filament protein in mature astrocytes and also an important component of the cytoskeleton in astrocytes during development. Abundance of GFAP positive cells (B) in brain tissue was determined through immunohistochemistry on perfuse brain tissue. Results are expressed as means±SEM (n=3-4 mice). Results expressed as percentage of total cells/field. Means without a common letter differ, P<0.1. Senescent mice had more abundance of GFAP$^+$ cells and SDP supplementation attenuates astrogliosis in aged mice with markers of cognitive impairment disorders.

Figure 18:
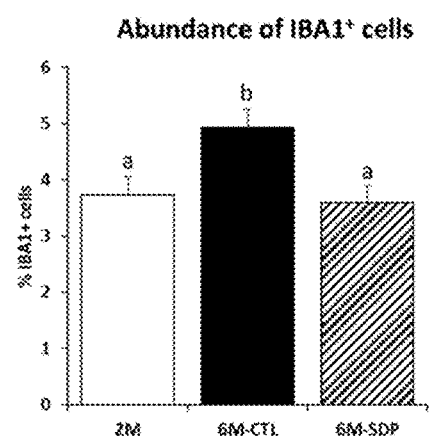
FIG. 18 provides the abundance (immunohistochemistry) of IBA1 in brain cells.

FIG. 18 shows the abundance in brain tissue of Ionized Calcium Binding Adaptor Molecule 1 (IBA1), which is a microglia/macrophage-specific calcium-binding protein and has the actin-bundling activity and participates in membrane ruffling and phagocytosis in activated microglia. Abundance of IBA1 positive cells in brain tissue was determined through immunohistochemistry on perfuse brain tissue. Results are expressed as means±SEM (n=3-4 mice). Results expressed as percentage of total cells/field. Means without a common letter differ, P<0.1. Senescent mice presented an activation of the microglia and SDP supplementation prevented it.

Figure 19:
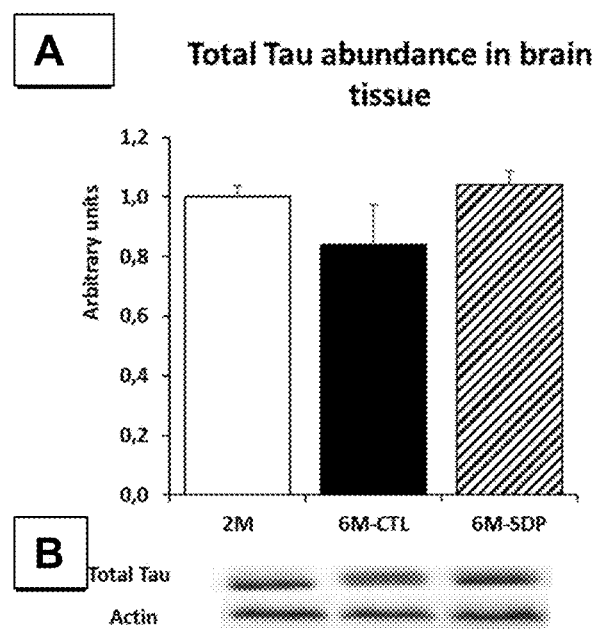
FIG. 19 provides the expression (Real-Time PCR) and abundance (Western Blot) of total Tau in brain tissue.
Figure 20:
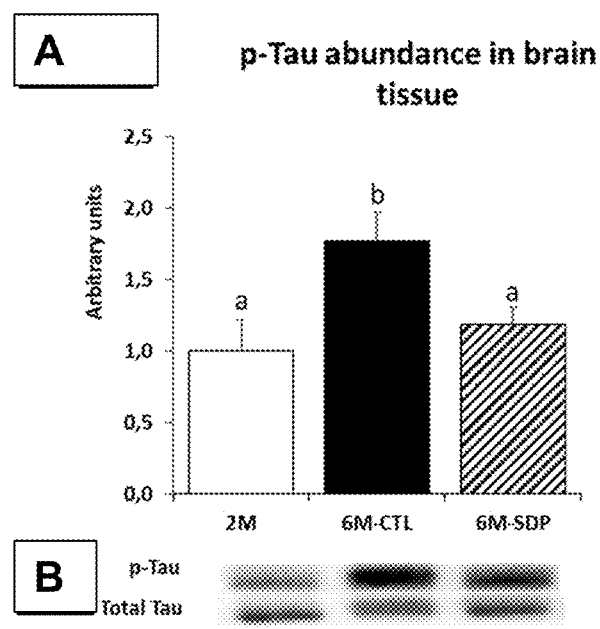
FIG. 20 provides the expression (Real-Time PCR) and abundance (Western Blot) of p-Tau in brain tissue.

FIG. 19 shows the expression and abundance in brain tissue of total Tau, which are microtubule-associated proteins (MAPs) and are abundant in neurons of the CNS. Several studies indicate that Tau protein plays an important role in the neurodegeneration observed in AD patients. Results are expressed as means±SEM (n=6-7 mice). FIG. 19A shows the results of Real-Time PCR. FIG. 19B shows representative images of the Western Blot of total Tau and β-actin (control). FIG. 20 shows the expression and abundance in brain tissue of hyperphosphorylation of Tau (p-Tau), which disrupts normal neuronal function in the regulation of axonal transport and leads to the accumulation of neurofibrillary tangles and toxic species of soluble tau and p-Tau also correlates with a cognitive decline. Results are expressed as means±SEM (n=6-7 mice). FIG. 20A shows the results of Real-Time PCR. Means without a common letter differ, P<0.1. FIG. 20B shows representative images of the Western Blot of p-Tau and total Tau. Aged SAMP8 mice showed increased abundance of the phosphorylated form of Tau (p-Tau), which is related to cognitive disorders. SDP supplementation reduced p-Tau formation during aging.

Figure 21:
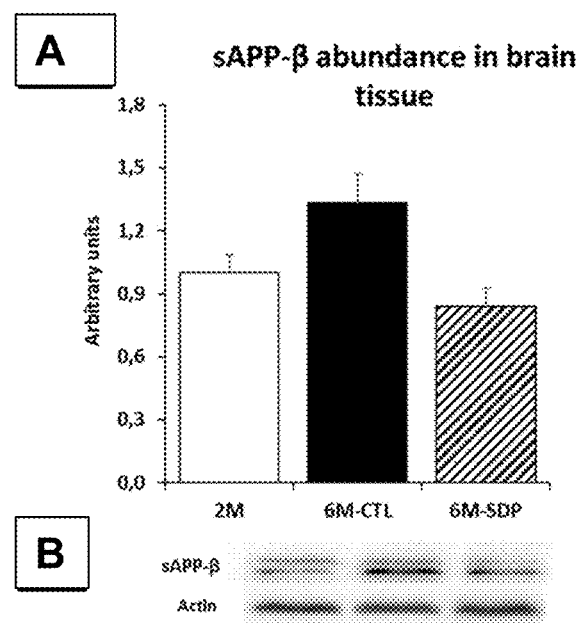
FIG. 21 provides the expression (Real-Time PCR) and abundance (Western Blot) of sAPP-β in brain tissue.
Figure 22:
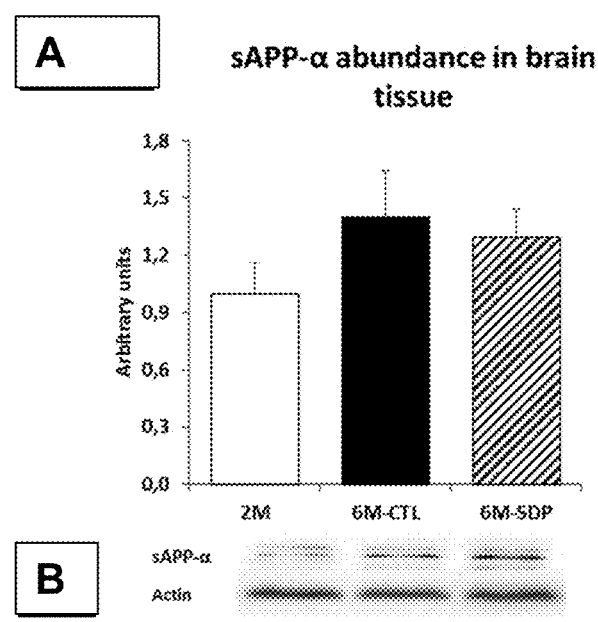
FIG. 22 provides the expression (Real-Time PCR) and abundance (Western Blot) of sAPP-α in brain tissue.

FIGS. 21 and 22 show the expression and abundance in brain tissue of sAPP-β and sAPP-α. Aβ42 is a peptide of β-amyloid protein that has high aggregative capacity and therefore forms senile aggregates and plaques in brain tissue that are responsible for the neuron degeneration observed in AD patients. This peptide originates by the cleavage of the amyloid precursor protein (APP) by the β-secretases. Senescent SAMP8 mice present an increase in APP production. Results are expressed as means±SEM (n=4-5 mice). FIGS. 21A and 22A show the results of Real-Time PCR in relation to sAPP-β and sAPP-α, respectively. FIGS. 21B and 22B show representative images of the Western Blot of β-actin (control) and sAPP-β and sAPP-α, respectively. The abundance of sAPP-R was increased in senescent mice. SDP supplementation prevented the accumulation of this protein. This observation suggests that this supplement has neuroprotective properties.

Figure 23:
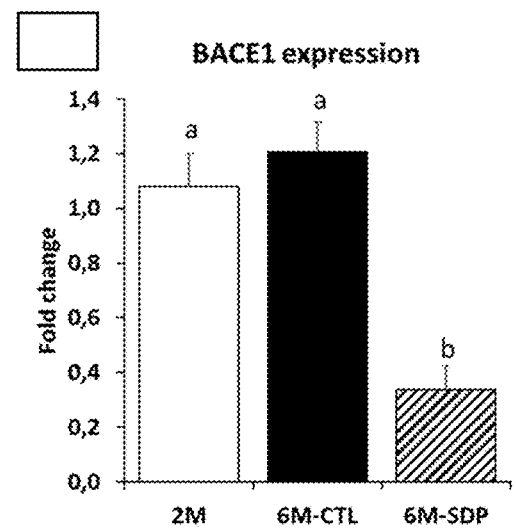
FIG. 23 provides the expression (Real-Time PCR) of BACE1 in brain tissue.

FIG. 23 shows the expression in brain tissue of BACE1, which is the p-secretase that participates in the production of the β-amyloid (Aβ42) peptide that is widely considered to have a crucial early role in the etiology of AD. Results are expressed as means±SEM (n=6-7 mice). Results of Real-Time PCR are shown. Means without a common letter differ, P<0.1. The expression of BACE1 was not affected by aging and SDP reduced its expression.

Figure 24:
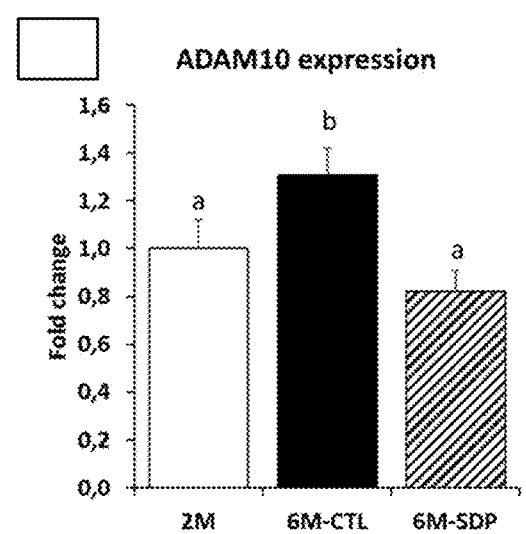
FIG. 24 provides the expression (Real-Time PCR) of ADAM10 in brain tissue.

FIG. 24 shows the expression in brain tissue of ADAM10, which is a protein that has been found in increased amounts in the hippocampal neurons of AD patients. Results are expressed as means±SEM (n=6-7 mice). Results of Real-Time PCR are shown. Means without a common letter differ, P<0.1. ADAM10 expression increased during aging and SDP prevented this age-dependent changes.

Conclusions:

Senescence is characterized by a reduction of neuronal dysfunction. SDP maintains neuronal integrity because it prevented the loss of pre- and post-synaptic connections associated with aging. In the CNS of aged SAMP8 mice there is an activation of microglia and astrogliosis. SDP supplementation prevented the activation of the microglia and astroglia. Aged SAMP8 mice showed increased abundance of the phosphorylated form of Tau (p-Tau) and the formation of the sAPP-β. Both proteins are related to cognitive disorders. SDP supplementation reduced p-Tau and sAPP-β during aging of SAMP8 mice.

SDP presents neuroprotective properties improving the cognitive functions of aged animals with markers of cognitive impairment disorders.

Example 5 (Prophetic)—Reduction in Severity of Cognitive Impairment Following Mild Traumatic Brain Injury in Individuals Consuming Plasma Proteins/Fractions The consumption of plasma, or plasma fractions, for 1-2 months prior to a TBI episode will lessen the severity of neurological and physiological changes resulting from TBI. The severity of neurological and physiological changes resulting from TBI includes both the magnitude of the absolute change in a measure and/or the time required for healing and subsequent improvement in neurological and physiological changes resultant from the TBI. Examples of animal models of TBI include the fluid percussion injury, cortical impact injury, weight drop-impact acceleration injury, and blast injury (Xiong Y, Mahmood A, Chopp M. Animal models of traumatic brain injury. *Nature reviews Neuroscience.* 2013; 14(2):128-142. doi:10.1038/nrn3407). Neurological processes such as motor function, alertness, seeking behavior, and recovery of short-term and long-term memory function would be improved for subjects consuming plasma proteins. Physiological parameters that would be improved include blood-brain barrier integrity, swelling, intracranial pressure, and reduced changes in specific biochemical markers of brain injury.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The invention claimed is:

1. A method of treating a cognitive impairment disorder in a human or companion animal subject, said method comprising:
   a. administering to said subject one or more cognitive functioning tests to identify a subject suffering from a cognitive impairment disorder; and
   b. orally administering to said subject a therapeutically effective amount of an animal plasma composition;
   wherein said administration provides an improvement in said subject's results in said one or more cognitive impairment tests.

2. The method of claim 1, wherein said animal plasma composition is derived from animal plasma from one or more animals selected from the group consisting of porcine, bovine, ovine, equine, and avian animals.

3. The method of claim 1, wherein said animal plasma composition is administered at a dose of 5 mg to 100 g per day.

4. The method of claim 1, wherein said animal plasma composition is administered at a dose of 500 mg to 5 g per day.

5. The method of claim 1, wherein said animal plasma composition is administered at a dose of 10 mg to 1 g per kg of body weight of the animal to be treated per day.

6. The method of claim 1, wherein said animal plasma composition is administered at a dose of 25-100 mg per kg of body weight of the animal to be treated per day.

7. The method of claim 1, wherein said animal plasma composition is administered for at least 3 months.

8. The method of claim 1, wherein said animal plasma composition is administered for at least 9 months.

9. The method of claim 1, wherein said animal plasma composition is administered for at least 12 months.

10. The method of claim 1, wherein said cognitive impairment disorder is selected from the group consisting of dementia disorders, concussion, and traumatic brain injury.

11. The method of claim 1, wherein said cognitive impairment disorder is a concussion.

12. The method of claim 1, wherein said cognitive impairment disorder is a traumatic brain injury.

13. The method of claim 1, wherein said cognitive impairment disorder is a dementia disorder.

14. The method of claim 1, wherein said cognitive impairment disorder is dementia resulting from Alzheimer's disease.

15. The method of claim 1, wherein said cognitive impairment disorder is dementia resulting from Parkinson's disease.

16. The method of claim 1, wherein said cognitive impairment disorder is vascular dementia.

17. The method of claim 1, wherein said subject is a companion animal selected from the group consisting of canine, feline, or equine.

18. The method of claim 1, wherein said subject is a human.

19. The method of claim 1, wherein said animal plasma composition is administered in food.

20. The method of claim 1, wherein said improvement in said subject's results in said one or more cognitive impairment tests comprises improved short term memory.

21. The method of claim 1, wherein said improvement in said subject's results in said one or more cognitive impairment tests comprises improved long term memory.

22. The method of claim 1, wherein said animal plasma composition comprises 70-90% by weight protein.

23. The method of claim 22, wherein said animal plasma composition comprises:
   i. about 1.0-6.0% by weight alpha-2 macroglobulin;
   j. about 1.0-5.5% by weight transferrin;
   k. about 0.1-1.0% by weight vitamin-D binding protein;
   l. about 0.1-2.0% by weight alpha-1-glycoprotein;
   m. about 5-30% by weight IgG;
   n. about 1.0-6.0% by weight IgA;
   o. about 0.5-5.0% by weight of IgM; and
   p. about 25-80%-by weight albumin.

24. The method of claim 23, wherein said animal plasma composition comprises:
   i. 2.0-3.5% by weight alpha-2 macroglobulin;
   j. 2.0-3.0% by weight transferrin;
   k. 0.3-0.45% by weight vitamin-D binding protein;
   l. 0.5-1.2% by weight alpha-1-glycoprotein;
   m. 10-20% by weight IgG;
   n. 1.5-3.25% by weight IgA;
   o. 0.75-3.0% by weight of IgM; and
   p. 40-50% by weight albumin.

25. The method of claim 1, said animal plasma composition comprises 90-95% by weight protein.

26. The method of claim 25, wherein said animal plasma composition comprises:
   i. about 1.0-9.0% by weight alpha-2 macroglobulin;
   j. about 2-18% by weight transferrin;
   k. about 0.1-1.0% by weight vitamin-D binding protein;
   l. about 0.1-2.0% by weight alpha-1-glycoprotein;
   m. about 25-75% by weight IgG;
   n. about 1.0-6.0% by weight IgA;
   o. about 2.5-10% by weight of IgM; and
   p. about 2.5-25% by weight albumin.

27. The method of claim 26, wherein said animal plasma composition comprises:

i. 3.0-6.0% by weight alpha-2 macroglobulin;
j. 4-10% by weight transferrin;
k. 0.25-0.6% by weight vitamin-D binding protein;
l. 0.4-1.3% by weight alpha-1-glycoprotein;
m. 40-65% by weight IgG;
n. 1.5-3.25% by weight IgA;
o. 3.5-7% by weight of IgM; and
p. 7-15% by weight albumin.

\* \* \* \* \*